United States Patent [19]

Kishino et al.

[11] 4,161,524

[45] Jul. 17, 1979

[54] O-ALKYL-S-N-PROPYL-N-SULFONYL-PHOSPHORIC ACID ESTER AMIDES

[75] Inventors: Shigeo Kishino; Junichi Saito, both of Tokyo; Akio Kudamatsu; Kozo Shiokawa, both of Kanagawa; Shinichi Tsuboi, Tokyo, all of Japan

[73] Assignee: Bayer Aktiengesellschaft, Leverkusen, Fed. Rep. of Germany

[21] Appl. No.: 917,719

[22] Filed: Jun. 21, 1978

Related U.S. Application Data

[62] Division of Ser. No. 723,834, Sep. 16, 1976, Pat. No. 4,134,979.

[30] Foreign Application Priority Data

Sep. 22, 1975 [JP] Japan .................... 50/113705

[51] Int. Cl.² .................... A01N 9/36; C07F 9/24
[52] U.S. Cl. .................... 424/215; 260/947
[58] Field of Search .................... 260/947; 424/215

Primary Examiner—Anton H. Sutto

Attorney, Agent, or Firm—Sprung, Felfe, Horn, Lynch & Kramer

[57] ABSTRACT

O-Alkyl-S-n-propyl-N-sulfonyl-phosphoric acid ester amides of the formula

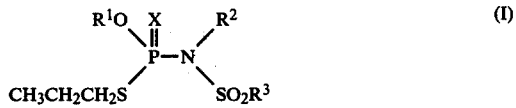

in which
R¹ is methyl or ethyl,
R² is $C_1$–$C_6$ alkyl or alkenyl, $C_1$–$C_6$ alkyl substituted by aryl, phenyl, $C_1$–$C_6$ alkylphenyl, or halophenyl
R³ is $C_1$–$C_6$ alkyl, $C_1$–$C_6$ alkyl substituted by halogen, phenyl, $C_1$–$C_6$ alkylphenyl, $C_1$–$C_6$ alkoxyphenyl, or nitrophenyl, and
X is oxygen or sulfur.

which possess insecticidal, acaricidal and nematicidal properties.

9 Claims, No Drawings

O-ALKYL-S-N-PROPYL-N-SULFONYL-PHOSPHORIC ACID ESTER AMIDES

This is a division of application Ser. No. 723,834, filed Sept. 16, 1976, now U.S. Pat. No. 4,134,979.

The present invention relates to and has for its objects the provision of particular new O-alkyl-S-n-propyl-N-sulfonylphosphoric acid ester amides, which possess insecticidal, acaricidal and nematicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

U.S. Pat. No. 3,716,600 discloses that a wide variety of compounds of the general formula

(VIII)

in which

R represents an alkyl group having 1 to 3 carbon atoms,

R' represents an aliphatic group having 1 to 3 carbon atoms,

R'' represents an alkyl group having 1 to 10 carbon atoms, a cycloalkyl group having 3 to 8 carbon atoms or a phenyl group, and Y represents an oxygen or sulfur atom, have insecticidal and acaricidal activities.

Hitherto, parathion has been widely used as an insecticide, for example for controlling rice borers, planthoppers and leafhoppers which are important insects that are harmful to rice. The use of parathion, however, has been suspended in some areas, particularly in Japan, because despite its excellent effectiveness against the pests, there is considered to be a great danger of its causing acute toxicity to mammals.

Furthermore, the long-term use of large amounts of organophosphorus compounds, such as parathion, EPH, BAYCID and Sumithion, organochlorine compounds, such as BHC and DDT, and carbamate compounds, such as Sevin, is bringing about the deplorable phenomenon that the pests are developing resistance to these chemicals.

Hence there is a need for new pesticides which have only a low toxicity to warm-blooded animals but which are effective against those pests that have attained resistance to prior-art pesticides.

The present invention provides phosphoric acid ester amides of the general formula

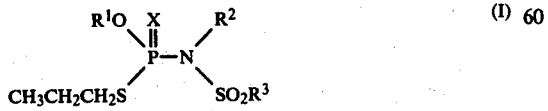

(I)

in which $R^1$ is methyl or ethyl, $R^2$ is $C_1$–$C_6$ alkyl or alkenyl, $C_1$–$C_6$ alkyl substituted by aryl, phenyl, $C_1$–$C_6$ alkylphenyl, or halophenyl $R^3$ is $C_1$–$C_6$ alkyl, $C_1$–$C_6$ alkyl substituted by halogen, phenyl, $C_1$–$C_6$ alkylphenyl, $C_1$–$C_6$ alkoxyphenyl, or nitrophenyl, and X is oxygen or sulfur.

It has been found that compounds of the formula (I) exhibit unusually strong insecticidal, acaricidal and nematicidal activities, and possess a higher effectiveness and a wider controlling effect than compounds of the formula (VIII); particularly, they have an excellent activity against spider mites that have attained resistance to various known organophosphorus pesticides.

Preferably, in formula (I), $R^2$ represents $C_1$–$C_4$ alkyl, an alkenyl radical selected from vinyl, allyl, propenyl and methallyl (allyl being especially preferred), an arylalkyl group selected from benzyl and 2-phenylethyl (benzyl being especially preferred), unsubstituted phenyl or a phenyl carrying one to three (especially one or two) substituents selected from chlorine and $C_1$–$C_4$ alkyl groups (especially methyl), and $R^3$ represents $C_1$–$C_4$ alkyl, halogenated $C_1$–$C_4$ alkyl for(example bromomethyl, 2-chloroethyl, 2-bromoethyl, 3-chloropropyl, 3-chlorobutyl, 4-chlorobutyl, 1-methyl-2-chloropropyl, 1-methyl-3-chloropropyl, 1-chloromethyl-ethyl, 1-chloromethyl-2-chloroethyl and, especially, chloromethyl), unsubstituted phenyl or phenyl carrying one to three substituents selected from $C_1$–$C_4$ alkyl (especially methyl), halogen (especially chlorine and bromine), $C_1$–$C_4$ alkoxy (especially methoxy) and nitro.

The present invention also provides a process for the preparation of a compound of the formula (I) in which (a) a phosphoramidothioate salt of the general formula

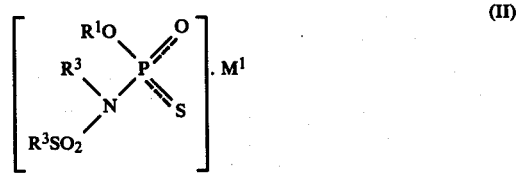

(II)

in which $R^1$, $R^2$ and $R^3$ have the meanings stated above, and $M^1$ is an alkali metal atom or an ammonium group, is reacted with an alkylating agent of the general formula

CH₃CH₂CH₂.Y  (III), in which

Y is a halogen atom or a sulfonic acid group, or (b) a thio (or dithio) phosphoryl halide of the general formula

(IV), in which $R^1$ and X have the meanings stated in claim 1 and Hal is halogen, is reacted with a sulfonamide salt of the general formula

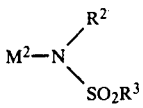

in which
R² and R³ have the meanings stated in claim 1 and
M² is an alkali metal atom.

The phosphoramidothioate salt (II) to be used in process variant (a) can be prepared by reacting a phosphoramidothioate of the general formula

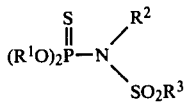

in which
R¹, R² and R³ have the meanings stated in claim 1, with a dealkylating agent of the general formula

in which
M¹ has the meaning given above, and
R⁴ is hydrogen, alkyl or alkoxythiocarbonyl.

Preferably, in the above formulas (II), (III) and (VII), M¹ represents a sodium or potassium atom, or an ammonium group; Y represents chlorine, bromine, iodine, fluorine, benzenesulfonate, p-toluenesulfonate, mono-propylsulfonate or sulfate; and R⁴ represents hydrogen, a $C_1$-$C_4$ alkyl group, methoxythiocarbonyl or ethoxythiocarbonyl.

Specific examples of the phosphoramidothioate salts of the formula (II) are as follows: potassium O-ethyl-N-methyl-N-methanesulfonylphosphoramidothioate, potassium O-ethyl-N-methyl-N-ethanesulfonylphosphoramidothioate, potassium O-ethyl-N-methyl-N-n-butanesulfonylphosphoramidothioate, potassium O-methyl-N-methyl-N-benzenesulfonylphosphoramidothioate, potassium O-ethyl-N-methyl-N-benzenesulfonylphosphoramidothioate, potassium O-ethyl-N-methyl-N-4-chlorobenzenesulfonylphosphoramidothioate, potassium O-ethyl-N-methyl-N-2,5-dichlorobenzenesulfonylphosphoramidothioate, potassium O-ethyl-N-methyl-N-4-methylbenzenesulfonylphosphoramidothioate, potassium O-ethyl-N-methyl-N-4-methoxybenzenesulfonylphosphoramidothioate, potassium O-ethyl-N-methyl-N-2-methoxy-5-chlorobenzenesulfonylphosphoramidothioate, potassium O-ethyl-N-methyl-N-2-nitrobenzenesulfonylphosphoramidothioate, potassium O-ethyl-N-ethyl-N-methanesulfonylphosphoramidothioate, potassium O-ethyl-N-iso-propyl-N-methanesulfonylphosphoramidothioate, potassium O-ethyl-N-iso-propyl-N-chloromethanesulfonylphosphoramidothioate, potassium O-ethyl-N-iso-propyl-N-benzenesulfonylphosphoramidothioate, potassium O-ethyl-N-n-butyl-N-methanesulfonylphosphoramidothioate, potassium O-ethyl-N-allyl-N-methanesulfonylphosphoramidothioate, potassium O-ethyl-N-allyl-N-benzenesulfonylphosphoramidothioate, potassium O-ethyl-N-phenyl-N-methanesulfonylphosphoramidothioate, potassium O-ethyl-N-phenyl-N-benzenesulfonylphosphoramidothioate, potassium O-ethyl-N-4-chlorophenyl-N-methanesulfonylphosphoramidothioate, potassium O-ethyl-N-4-methylphenyl-N-methanesulfonylphosphoramidothioate, potassium O-ethyl-N-(2-methyl-4-chlorophenyl)-N-methanesulfonylphosphoramidothioate, potassium O-ethyl-N-benzyl-N-methanesulfonylphosphoramidothioate, potassium O-methyl-N-methyl-N-methanesulfonylphosphoramidothioate, potassium O-ethyl-N-2-methylphenyl-N-methanesulfonylphosphoramidothioate, potassium O-ethyl-N-2,4-dimethylphenyl-N-methanesulfonylphosphoramidothioate, potassium O-ethyl-N-2,4-dichlorophenyl-N-methanesulfonylphosphoramidothioate, potassium O-ethyl-N-(2-methyl-4-chlorophenyl)-N-benzenesulfonylphosphoramidothioate, potassium O-ethyl-N-methyl-N-chloromethanesulfonylphosphoramidothioate, potassium O-ethyl-N-methyl-N-4-bromobenzenesulfonylphosporamidothioate, and potassium O-ethyl-N-methyl-N-2,4,5-trichlorobenzenesulfonylphosphoramidothioate, as well as the corresponding sodium salts, triethylammonium salts, dimethylanilinium salts and pyridinium salts.

Specific examples of the alkylating agents of the formula (III) are as follows: n-propylchloride, n-propyl bromide, n-propyl benzene sulfonate, n-propyl-p-toluene sulfonate, di-n-propyl sulfate, and mono-n-propyl sulfate.

Examples of the phosphoramidothioates of the formula (VI) are as follows: O,O-di-ethyl-N-methyl-N-methanesulfonylphosphoramidothioate, O,O-di-ethyl-N-methyl-N-ethanesulfonylphosphoramidothioate, O,O-di-ethyl-N-methyl-N-n-butanesulfonylphosphoramidothioate, O,O-di-methyl-N-methyl-N-benzenesulfonylphosphoramidothioate, O,O-di-ethyl-N-methyl-N-benzenesulfonylphosphoramidothioate, O,O-di-ethyl-N-methyl-N-4-chlorobenzenesulfonylphosphoramidothioate, O,O-di-ethyl-N-methyl-N-2,5-dichlorobenzenesulfonylphosphoramidothioate, O,O-di-ethyl-N-methyl-N-4-methylbenzenesulfonylphosphoramidothioate, O,O-di-ethyl-N-methyl-N-4-methoxybenzenesulfonylphosphoramidothioate, O,O-di-ethyl-N-methyl-N-2-methoxy-5-chlorobenzenesulfonylphosphoramidothioate, O,O-di-ethyl-N-methyl-N-2-nitrobenzenesulfonylphosphoramidothioate, O,O-di-ethyl-N-ethyl-N-methanesulfonylphosphoramidothioate, O,O-di-ethyl-N-iso-propyl-N-methanesulfonylphosphoramidothioate, O,O-di-ethyl-N-iso-propyl-N-chloromethanesulfonylphosphoramidothioate, O,O-di-ethyl-N-iso-propyl-N-benzenesulfonylphosphoramidothioate, O,O-di-ethyl-N-n-butyl-N-methanesulfonylphosphoramidothioate, O,O-di-ethyl-N-allyl-N-methanesulfonylphosphoramidothioate, O,O-di-ethyl-N-allyl-N-benzenesulfonylphosphoramidothioate, O,O-di-ethyl-N-phenyl-N-methanesulfonylphosphoramidothioate, O,O-di-ethyl-N-phenyl-N-benzenesulfonylphosphoramidothioate, O,O-di-ethyl-N-4-chlorophenyl-N-methanesulfonylphosphoramidothioate, O,O-di-ethyl-N-4-methylphenyl-N-methanesulfonylphosphoramidothioate, O,O-di-ethyl-N-(2-methyl-4-chlorophenyl)-N-methanesulfonylphosphoramidothioate, O,O-di-ethyl-N-benzyl-N-methanesulfonylphosphoramidothioate, O,O-di-methyl-N-methyl-N-methanesulfonylphosphoramidothioate, O,O-di-ethyl-N-2-methylphenyl-N-methanesulfonylphosphoramidothioate, O,O-di-ethyl-N-2,4-dimethylphenyl-N-methanesulfonylphosphoramidothioate, O,O-di-ethyl-N-2,4-dichlorophenyl-N-methanesulfonylphosphoramidothioate, O,O-di-ethyl-N-(2-methyl-4-chlorophenyl)-N-benzenesulfonylphosphoramidothioate, O,O-di-ethyl-N-methyl-N-chloromethanesulfonylphosphoramidothioate, O,O-di-ethyl-N-methyl-N-4- bromobenzenesulfonylphosphoramidothioate, and O,O-di-ethyl-N-methyl-N-2,4,5-trichlorobenzenesulfonyl-phosphoramidothioate.

Examples of the dealkylating agents of the formula (VII) are as follows: sodium hydrosulfide, potassium hydrosulfide, sodium methanethiolate, potassium ethanethiolate, sodium 2-propanethiolate, potassium methylxanthogenate, potassium ethylxanthogenate, and ammonium sulfide.

The process variant (a) is illustrated by the following reaction scheme:

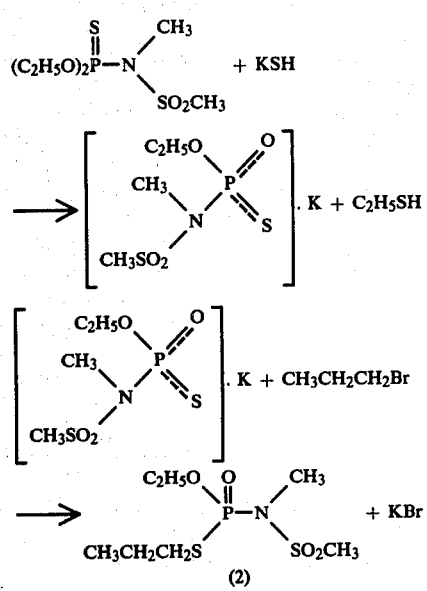

In the above sequence, the potassium O-ethyl-N-methyl-N-methanesulfonylphosphoramidothioate obtained in the first step may be isolated. However, it is also possible to react it in situ, i.e. without isolation, with the alkylating agent to obtain the desired O-ethyl-S-n-propyl-N-methyl-N-methanesulfonylphosphoramidothioate of a high purity and in a high yield.

The process variant (a) of the present invention is carried out preferably using a solvent or diluent. Examples of such solvents or diluents are water and inert organic solvents selected from aliphatic, alicyclic and aromatic hydrocarbons which optionally may be chlorinated, such as hexane, cyclohexane, petroleum ether, ligroin, benzene, toluene, xylene, methylene chloride, chloroform, carbon tetrachloride, ethylene chloride, trichloroethylene and chlorobenzene; ethers, such as diethyl ether, methylethyl ether, diisopropyl ether, dibutyl ether, propylene oxide, dioxane and tetrahydrofuran; ketones, such as acetone, methyl ethyl ketone, methyl isopropyl ketone and methyl isobutyl ketone; nitriles, such as acetonitrile, propionitrile and acrylonitrile; alcohols, such as methanol, ethanol, isopropanol, tert.-butanol and ethylene glycol; esters, such as ethyl acetate and amyl acetate; acid amides, such as dimethylformamide; sulfones and sulfoxides, such as dimethyl sulfoxide and dimethyl sulfone; and bases, such as pyridine.

The process variant (b) of the present invention can be performed in a wide temperature range. In general, the process is carried out at a temperature between −20° C. and the boiling point of the mixture, preferably at a temperature of from 0° to 100° C. Furthermore, the reaction is carried out preferably at atmospheric pressure, although it can also be performed under an elevated or reduced pressure.

Referring now to process variant (b), in the general formulas (IV) and (V), Hal preferably represents a chlorine atom; and $M^2$ preferably represents potassium or sodium.

Specific examples of the thio(or dithio)phosphoryl halides of the formula (IV) are as follows: O-methyl-S-n-propylthiophosphoryl chloride, O-ethyl-S-n-propylthiophosphoryl chloride, O-methyl-S-n-propyldithiophosphoryl chloride, and O-ethyl-S-n-propyldithiophosphoryl chloride.

Specific examples of the sulfonamide salts of the formula (V) are as follows: sodium N-methylmethanesulfonamide, sodium N-methylethanesulfonamide, sodium N-methyl-n-butanesulfonamide, sodium N-methylbenzenesulfonamide, sodium N-methyl-4-chlorobenzenesulfonamide, sodium N-methyl-2,5-dichlorobenzenesulfonamide, sodium N-methyl-4-methylbenzenesulfonamide, sodium N-methyl-4-methoxybenzenesulfonamide, sodium N-methyl-2-methoxy-5-chlorobenzenesulfonamide, sodium N-methyl-2-nitrobenzenesulfonamide, sodium N-ethylmethanesulfonamide, sodium N-iso-propylmethanesulfonamide, sodium N-isopropylchloromethanesulfonamide, sodium N-iso-propylbenzenesulfonamide, sodium N-n-butylmethanesulfonamide, sodium N-allylmethanesulfonamide, sodium N-allylbenzenesulfonamide, sodium methanesulfonanilide, sodium benzenesulfonanilide, sodium methanesulfone-4-chloroanilide, sodium methanesulfon-4-methylanilide, sodium methanesulfon-2-methyl-4-chloroanilide, sodium N-benzylmethanesulfonamide, sodium methanesulfon-2-methylanilide, sodium methanesulfon-2,4-dimethylanilide, sodium methanesulfon-2,4-dichloroanilide, sodium methanesulfon-2-methyl-4-chloroanilide, sodium N-methylchloromethanesulfonamide, sodium N-methyl-4-bromobenzenesulfonamide, and sodium N-methyl-2,4,5-trichlorobenzenesulfonamide, and the corresponding potassium salts.

The process variant (b) is illustrated by the following two reaction schemes:

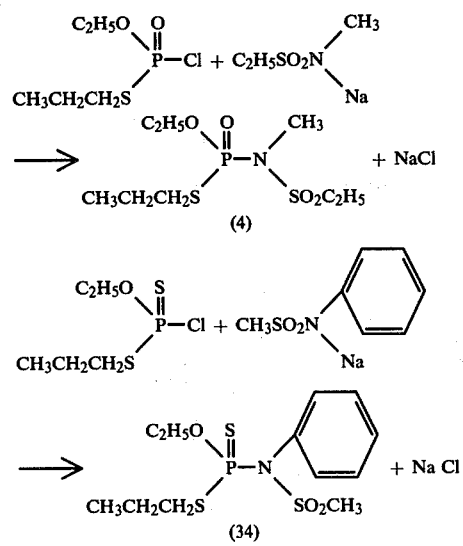

In carrying out process variant (b) an inert solvent or diluent is preferably used. The solvents mentioned above in connection with process variant (a) may be used to obtain the desired product in a high purity and in a high yield.

A wide range of temperature can be employed in process variant (b). Generally, the reaction is effected at a temperature between −20° C. and the boiling point of the mixture, preferably at from 0° to 100° C. Although it is desirable for the reaction to be carried out at atmospheric pressure, it is also possible to perform the reaction under an elevated or reduced pressure.

As already mentioned, the phosphoric acid ester amides according to the invention are distinguished by an excellent insecticidal, acaricidal and nematicidal activity. They are active against plant pests, pests harmful to health and pests of stored products, for example grain, and combine a low phytotoxicity with a good action against both sucking and biting insects and against mites; the action sets in quickly and is long-lasting.

For these reasons, the compounds according to the invention can be employed successfully as pesticides in plant protection and also in the hygiene field and the field of protection of stored products. In the field of veterinary medicine, the present compounds are effective against various endoparasites and ectoparasites, such as ticks and insects.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

Also to be classed with the biting insects are beetles (Coleoptera), for example the granary weevil (*Sitophilus granarius=Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius=Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta Americana*), Medeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domesticus*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aëdes aegypti*), the northern house mosquito (*Culex pipiens*) and the malaria mosquito (*Anopheles stephensi*).

With the mites (Acarina) there are classed, in particular, the spider mites (Tetranychidae) such as the two-spotted spider mite (*Tetranychus urticae*) and the European red mite (*Paratetranychus pilosus=Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the novel products are also distinguished by an outstanding residual activity on wood and clay, as well as a good stability to alkali on limed substrates.

The active compounds according to the invention couple a low toxicity to warm-blooded animals with powerful nematicidal properties and can therefore be used to combat nematodes, especially phytopathogenic nematodes. These essentially include leaf nematodes (Arphelenchoides), such as the crysanthemam eelworm (*A. ritzemabosi*), the leafblotch eelworm (*A. fragariae*) and the rice eelworm (*A. oryzae*); stem nematodes (Ditylenchus), such as the stem eelworm (*D. Dipsaci*); root-knot nematodes (Meloidogvne), such as *M. arenaria* and *M. incognita*; cyst-forming nematodes (Heterodera), such as the potato cyst eelworm (*H. rostochiensis*) and the beet cyst eelworm (*H. schachtii*); and also free-living root nematodes, for example of the genera Pratylenchus, Paratylenchus, Rotylenchus, Xiphinema and Radopholus.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other nematocides, insecticides, acaricides and fungicides, or bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–20%, preferably 0.005–10% by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.0005–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When applied to areas of agriculture and particularly when used against nematodes, the preparations are generally applied in amounts of 1 to 100 kg of active compound per hectare, particularly 30 g to 10 kg and especially 300 g to 6 kg per hectare, and are then incorporated into the soil.

Furthermore, the present invention contemplates methods of selectively killing, combating or controlling pests, e.g. insects, acarids and nematodes, which comprises applying to at least one of correspondingly (a) such insects, (b) such acarids, (c) such nematodes and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE (i)

A wettable powder was prepared by pulverizing and mixing 15 parts of compound No. 6, 80 parts of a mixture (1:5) of diatomaceous earth and kaolin, and 5 parts of an emulsifier RUNNOX (a product of Toho Kagaku Kogyo Kabushiki Kaisha, polyoxyethylenealkyl phenyl ether). This could be diluted with water to 0.05% before application by spraying.

EXAMPLE (ii)

An emulsifiable concentrate was prepared by mixing and stirring 30 parts of compound No. 2, 30 parts of xylene, 30 parts of KAWAKAZOL (methylnaphthalene, a product of Kawasaki Kasei Chemicals Limited) and 10 parts of SORPOL (polyoxyethylene alkylphenyl ether, a product of Toho Kagaku Kogyo Kabushiki Kaisha). This could be diluted with water to 0.05% before spraying.

EXAMPLE (iii)

A dusting agent was prepared by pulverizing and mixing 2 parts of compound No. 8 and 98 parts of a mixture (1:3) of talc and clay. This could be applied by scattering.

EXAMPLE (iv)

A dusting agent was prepared by pulverizing and mixing 1.5 parts of compound No. 3, 0.5 part of isopropyl hydrogen phosphate (PAP), and 98 parts of a mixture (1:3) of talc and clay.

EXAMPLE (v)

10 parts of compound No. 4, 10 parts of bentonite, 78 parts of a mixture (1:3) of talc and clay, and 2 parts of lignin sulfonate were mixed. 25 parts of water were added to the mixture. The whole was mixed thoroughly and then processed with an extrusion granulator into granules of 20 to 40 mesh, which were dried at 40°–50° C.

EXAMPLE (vi)

95 parts of clay powder having a particle size distribution of 0.2 to 2 mm were placed in a rotary mixer. During rotation, there were sprayed over the particles 5 parts of a solution of compound No. 26 in an organic solvent, thereby wetting them uniformly. Then, drying at 40° to 50° C. was effected in order to form granules.

EXAMPLE (vii)

An oil preparation was prepared by mixing and stirring 0.5 part of compound No. 18, 20 parts of VELSICOL AR-50 (high-boiling aromatic compounds, a product of Velsicol Chem. Co.) and 79.5 parts of kerosine.

The insecticidal, acaricidal and nematicidal activity of the compounds of this invention is illustrated by the following biotest Examples.

EXAMPLE 1

Test on larvae of *Prodenia litura Fabricius*
Solvent: xylol, 3 parts by weight
Emulsifier: polyoxyethylene alkylphenylether, 1 part by weight To form a suitable preparation of the active compound, 1 part by weight of the active compound was mixed with the above amount of the solvent containing the above amount of the emulsifier, and the mixture was diluted with water to a predetermined concentration.

Sweet potato leaves were dipped in an aqueous preparation, of a predetermined concentration, of the active compound. After drying in the air, the leaves were placed in a Petri dish 9 cm. in diameter. Then, 10 third instar larvae of *Prodenia litura Fabricius* were placed in the Petri dish. The dish was placed in a constant-temperature room at 28° C. Twenty-four hours later, the number of dead larvae was determined in order to calculate the kill ratio. The results are shown in Table 1.

TABLE 1

| Compound No. | Kill ratio (%) at a concentration of (ppm) | | | |
|---|---|---|---|---|
| | 1000 | 300 | 100 | 50 |
| 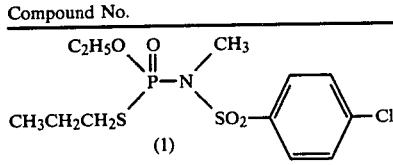 (1) | 100 | 100 | 100 | |
| 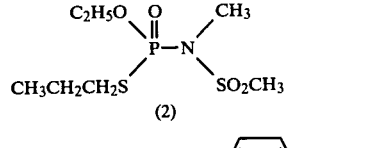 (2) | 100 | 100 | 100 | 100 |
| 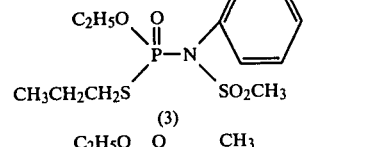 (3) | 100 | 100 | 100 | 100 |
| 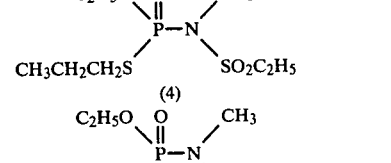 (4) | 100 | 100 | 100 | |
| 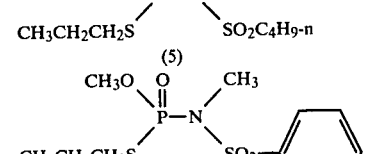 (5) | 100 | 100 | 100 | 100 |
|  (6) | 100 | 100 | 100 | 100 |

TABLE 1-continued

| Compound No. | Kill ratio (%) at a concentration of (ppm) | | | |
|---|---|---|---|---|
| | 1000 | 300 | 100 | 50 |
| (7) $C_2H_5O$, $CH_3CH_2CH_2S$ — P(=O) — N(CH_3) — SO_2—C_6H_5 | 100 | 100 | | |
| (8) $C_2H_5O$, $CH_3CH_2CH_2S$ — P(=O) — N(CH_3) — SO_2—(2-Cl,5-Cl-C_6H_3) | 100 | 100 | 100 | |
| (9) $C_2H_5O$, $CH_3CH_2CH_2S$ — P(=O) — N(CH_3) — SO_2—C_6H_4—CH_3 | 100 | 100 | 100 | |
| (11) $C_2H_5O$, $CH_3CH_2CH_2S$ — P(=O) — N(CH_3) — SO_2—(2-OCH_3,5-Cl-C_6H_3) | 100 | 100 | | |
| (12) $C_2H_5O$, $CH_3CH_2CH_2S$ — P(=O) — N(CH_3) — SO_2—(2-NO_2-C_6H_4) | 100 | 100 | 100 | |
| (13) $C_2H_5O$, $CH_3CH_2CH_2S$ — P(=O) — N(C_2H_5) — SO_2CH_3 | 100 | 100 | 100 | |
| (14) $C_2H_5O$, $CH_3CH_2CH_2S$ — P(=O) — N(i-C_3H_7) — SO_2CH_3 | 100 | 100 | 100 | |
| (15) $C_2H_5O$, $CH_3CH_2CH_2S$ — P(=O) — N(C_3H_7-iso) — SO_2CH_2Cl | 100 | 100 | 100 | |
| (17) $C_2H_5O$, $CH_3CH_2CH_2S$ — P(=O) — N(C_4H_9-n) — SO_2CH_3 | 100 | 100 | 100 | |
| (18) $C_2H_5O$, $CH_3CH_2CH_2S$ — P(=O) — N(CH_2CH=CH_2) — SO_2CH_3 | 100 | 100 | 100 | 100 |
| (19) $C_2H_5O$, $CH_3CH_2CH_2S$ — P(=O) — N(CH_2CH=CH_2) — SO_2—C_6H_5 | 100 | 100 | 100 | |

TABLE 1-continued

| Compound No. | Kill ratio (%) at a concentration of (ppm) | | | |
|---|---|---|---|---|
| | 1000 | 300 | 100 | 50 |
| (20) $C_2H_5O$, $P(=O)$, $CH_3CH_2CH_2S$ — N(phenyl)(SO$_2$-phenyl) | 100 | 100 | 100 | |
| (21) $C_2H_5O$, $P(=O)$, $CH_3CH_2CH_2S$ — N(4-Cl-phenyl)(SO$_2CH_3$) | 100 | 100 | 100 | 100 |
| (22) $C_2H_5O$, $P(=O)$, $CH_3CH_2CH_2S$ — N(4-CH$_3$-phenyl)(SO$_2CH_3$) | 100 | 100 | 100 | |
| (23) $C_2H_5O$, $P(=O)$, $CH_3CH_2CH_2S$ — N(2-CH$_3$-4-Cl-phenyl)(SO$_2CH_3$) | 100 | 100 | 100 | 100 |
| (24) $C_2H_5O$, $P(=O)$, $CH_3CH_2CH_2S$ — N(CH$_2$-phenyl)(SO$_2CH_3$) | 100 | 100 | 100 | 100 |
| (25) $C_2H_5O$, $P(=S)$, $CH_3CH_2CH_2S$ — N(CH$_3$)(SO$_2CH_3$) | 100 | 100 | | |
| (26) $C_2H_5O$, $P(=S)$, $CH_3CH_2CH_2S$ — N(CH$_3$)(SO$_2C_2H_5$) | 100 | 100 | 100 | |
| (28) $C_2H_5O$, $P(=S)$, $CH_3CH_2CH_2S$ — N(CH$_3$)(SO$_2$-4-Cl-phenyl) | 100 | 100 | 100 | |
| (29) $C_2H_5O$, $P(=S)$, $CH_3CH_2CH_2S$ — N(CH$_3$)(SO$_2$-2,5-diCl-phenyl) | 100 | 100 | 100 | |
| (30) $C_2H_5O$, $P(=S)$, $CH_3CH_2CH_2S$ — N(C$_2H_5$)(SO$_2CH_3$) | 100 | 100 | 100 | |

TABLE 1-continued

| Compound No. | Kill ratio (%) at a concentration of (ppm) | | | |
|---|---|---|---|---|
| | 1000 | 300 | 100 | 50 |
| (32) $C_2H_5O$, $S$ / $P-N$ / $CH_3CH_2CH_2S$ $SO_2CH_3$ ; N-substituent: $CH_2CH=CH_2$ | 100 | 100 | 100 | |
| (34) $C_2H_5O$, $S$ / $P-N$(phenyl) / $CH_3CH_2CH_2S$ $SO_2CH_3$ | 100 | 100 | | |
| (35) $CH_3O$, $O$ / $P-N-CH_3$ / $CH_3CH_2CH_2S$ $SO_2CH_3$ | 100 | 100 | 100 | |
| (36) $C_2H_5O$, $O$ / $P-N$(2-methylphenyl) / $CH_3CH_2CH_2S$ $SO_2CH_3$ | 100 | 100 | 100 | |
| (37) $C_2H_5O$, $O$ / $P-N$(2,4-dimethylphenyl) / $CH_3CH_2CH_2S$ $SO_2CH_3$ | 100 | 100 | 100 | |
| (38) $C_2H_5O$, $O$ / $P-N$(2,4-dichlorophenyl) / $CH_3CH_2CH_2S$ $SO_2CH_3$ | 100 | 100 | | |
| (39) $C_2H_5O$, $O$ / $P-N$(2-methyl-4-chlorophenyl) / $CH_3CH_2CH_2S$ $SO_2$(phenyl) | 100 | 100 | 100 | |
| (40) $C_2H_5O$, $O$ / $P-N-CH_3$ / $CH_3CH_2CH_2S$ $SO_2CH_2Cl$ | 100 | 100 | 100 | |
| (41) $C_2H_5O$, $O$ / $P-N-CH_3$ / $CH_3CH_2CH_2S$ $SO_2$(4-bromophenyl) | 100 | 100 | 100 | |
| (42) $C_2H_5O$, $O$ / $P-N-CH_3$ / $CH_3CH_2CH_2S$ $SO_2$(2,4,5-trichlorophenyl) | 100 | 100 | 100 | |

TABLE 1-continued

| Compound No. | Kill ratio (%) at a concentration of (ppm) | | | |
|---|---|---|---|---|
| | 1000 | 300 | 100 | 50 |
| (A) n-C$_3$H$_7$O\\P(=O)—NHSO$_2$CH$_3$ / n-C$_3$H$_7$S | 0 | | | |
| (B) n-C$_3$H$_7$O\\P(=O)—NHSO$_2$—C$_6$H$_5$ / n-C$_3$H$_7$S | 0 | | | |
| (C) (C$_2$H$_5$O)$_2$P(=O)—N(CH$_3$)(SO$_2$C$_6$H$_5$) | 0 | | | |
| (D) (C$_2$H$_5$O)$_2$P(=O)—N(C$_3$H$_7$-iso)(SO$_2$C$_2$H$_5$) | 30 | 0 | | |
| (E) (C$_2$H$_5$O)$_2$P(=O)—N(C$_2$H$_5$)(SO$_2$CH$_3$) | 50 | 0 | | |

EXAMPLE 2

Test on *Nephotettix cincticeps*

Rice plants each about 10 cm. in height were planted in pots each 12 cm. in diameter. On to the rice plants there was applied an aqueous preparation, at a predetermined concentration, of the active compound (prepared as in Example 1) at a rate of 10 ml. per pot. After drying the applied preparation, wire-gauze cages each 7 cm. in diameter and 14 cm. in height were placed over the pots, into which cages 30 female imagos of *Nephotettix cincticeps* were released. The pots were then placed in a constant-temperature room and, 24 hours later, the number of dead insects was determined in order to calculate the kill ratio. The results are shown in Table 2.

TABLE 2

| Compound No. | Kill ratio (%) at a concentration of | | |
|---|---|---|---|
| | 1000 | 100 | 50 (ppm) |
| (2) C$_2$H$_5$O\\P(=O)—N(CH$_3$)(SO$_2$CH$_3$) / CH$_3$CH$_2$CH$_2$S | 100 | 100 | |
| (3) C$_2$H$_5$O\\P(=O)—N(C$_6$H$_5$)(SO$_2$CH$_3$) / CH$_3$CH$_2$CH$_2$S | 100 | 100 | |
| (4) C$_2$H$_5$O\\P(=O)—N(CH$_3$)(SO$_2$C$_2$H$_5$) / CH$_3$CH$_2$CH$_2$S | 100 | 100 | |

| Compound No. | Kill ratio (%) at a concentration of | |
|---|---|---|
| | 1000 | 100 (ppm) |
| (6) CH$_3$O\\P(=O)—N(CH$_3$)(SO$_2$C$_6$H$_5$) / CH$_3$CH$_2$CH$_2$S | 100 | 100 |

TABLE 2-continued

| Compound | Col1 | Col2 |
|---|---|---|
| (7) C₂H₅O, CH₃CH₂CH₂S–P(=O)–N(CH₃)–SO₂–C₆H₅ | 100 | 100 |
| (12) C₂H₅O, CH₃CH₂CH₂S–P(=O)–N(CH₃)–SO₂–C₆H₄(o-NO₂) | 100 | 100 |
| (13) C₂H₅O, CH₃CH₂CH₂S–P(=O)–N(C₂H₅)–SO₂CH₃ | 100 | 100 |
| (14) C₂H₅O, CH₃CH₂CH₂S–P(=O)–N(iso-C₃H₇)–SO₂CH₃ | 100 | 100 |
| (15) C₂H₅O, CH₃CH₂CH₂S–P(=O)–N(iso-C₃H₇)–SO₂CH₂Cl | 100 | 100 |
| (17) C₂H₅O, CH₃CH₂CH₂S–P(=O)–N(n-C₄H₉)–SO₂CH₃ | 100 | 100 |
| (18) C₂H₅O, CH₃CH₂CH₂S–P(=O)–N(CH₂CH=CH₂)–SO₂CH₃ | 100 | 100 |
| (19) C₂H₅O, CH₃CH₂CH₂S–P(=O)–N(CH₂CH=CH₂)–SO₂–C₆H₅ | 100 | 100 |
| (20) C₂H₅O, CH₃CH₂CH₂S–P(=O)–N(C₆H₅)–SO₂–C₆H₅ | 100 | 100 |
| (21) C₂H₅O, CH₃CH₂CH₂S–P(=O)–N(C₆H₄-4-Cl)–SO₂CH₃ | 100 | 100 |
| (24) C₂H₅O, CH₃CH₂CH₂S–P(=O)–N(CH₂C₆H₅)–SO₂CH₃ | 100 | 100 |
| (30) C₂H₅O, CH₃CH₂CH₂S–P(=S)–N(C₂H₅)–SO₂CH₃ | 100 | 100 |

TABLE 2-continued

| Structure | | |
|---|---|---|
| (35) CH₃O, O, CH₃CH₂CH₂S–P(=O)–N(CH₃)(SO₂CH₃) | 100 | 100 |
| (36) C₂H₅O, CH₃CH₂CH₂S–P(=O)–N(SO₂CH₃)(o-tolyl) | 100 | 100 |
| (39) C₂H₅O, CH₃CH₂CH₂S–P(=O)–N(SO₂C₆H₅)(2-methyl-4-chlorophenyl) | 100 | 100 |
| (40) C₂H₅O, CH₃CH₂CH₂S–P(=O)–N(CH₃)(SO₂CH₂Cl) | 100 | 100 |
| (A) n-C₃H₇O, n-C₃H₇S–P(=O)–NHSO₂CH₃ | 40 | 0 |
| (B) n-C₃H₇O, n-C₃H₇S–P(=O)–NHSO₂C₆H₅ | 40 | 0 |
| (C) (C₂H₅O)₂P(=O)–N(CH₃)(SO₂C₆H₅) | 50 | 0 |
| (D) (C₂H₅O)₂P(=O)–N(iso-C₃H₇)(SO₂C₂H₅) | 100 | 0 |
| (E) (C₂H₅O)₂P(=O)–N(C₂H₅)(SO₂CH₃) | 100 | 0 |

EXAMPLE 3

Test on *Callosobruchus chinensis*

The bottom of a Petri dish 9 cm. in diameter was covered with a filter paper, onto which was placed 1 ml. of an aqueous preparation, at a predetermined concentration, of the active compound (prepared as in Example 1). 20 *Callosobruchus chinensis* beetles were placed therein, and the Petri dish was allowed to stand in a constant-temperature room at 28° C. for 24 hours. After 24 hours had elapsed, the number of dead beetles was determined in order to calculate the kill ratio. The results are shown in Table 3.

TABLE 1

| Compound No. | Kill ratio (%) at a concentration of (ppm) | | |
|---|---|---|---|
| | 1000 | 100 | 10 |
| (2) $C_2H_5O$, $CH_3CH_2CH_2S$ — P(=O) — N(CH_3)(SO_2CH_3) | 100 | 100 | |
| (4) $C_2H_5O$, $CH_3CH_2CH_2S$ — P(=O) — N(CH_3)(SO_2C_2H_5) | 100 | 100 | 100 |
| (8) $C_2H_5O$, $CH_3CH_2CH_2S$ — P(=O) — N(CH_3)(SO_2-2,5-Cl_2C_6H_3) | 100 | 100 | |
| (13) $C_2H_5O$, $CH_3CH_2CH_2S$ — P(=O) — N(C_2H_5)(SO_2CH_3) | 100 | 100 | |
| (17) $C_2H_5O$, $CH_3CH_2CH_2S$ — P(=O) — N(n-C_4H_9)(SO_2CH_3) | 100 | 100 | |
| (18) $C_2H_5O$, $CH_3CH_2CH_2S$ — P(=O) — N(CH_2CH=CH_2)(SO_2CH_3) | 100 | 100 | |
| (19) $C_2H_5O$, $CH_3CH_2CH_2S$ — P(=O) — N(CH_2CH=CH_2)(SO_2C_6H_5) | 100 | 100 | |
| (20) $C_2H_5O$, $CH_3CH_2CH_2S$ — P(=O) — N(C_6H_5)(SO_2C_6H_5) | 100 | 100 | |
| (21) $C_2H_5O$, $CH_3CH_2CH_2S$ — P(=O) — N(4-ClC_6H_4)(SO_2CH_3) | 100 | 100 | |
| (25) $C_2H_5O$, $CH_3CH_2CH_2S$ — P(=S) — N(CH_3)(SO_2CH_3) | 100 | 100 | 100 |
| (26) $C_2H_5O$, $CH_3CH_2CH_2S$ — P(=S) — N(CH_3)(SO_2C_2H_5) | 100 | 100 | |

TABLE 1-continued
| Compound No. | Kill ratio (%) at a concentration of (ppm) | | |
|---|---|---|---|
| | 1000 | 100 | 10 |
| (27) 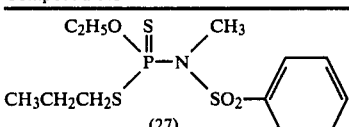 | 100 | 100 | |
| (28) 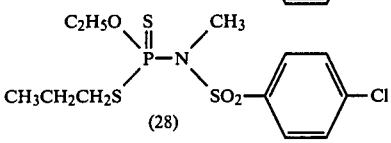 | 100 | 100 | |
| (29) 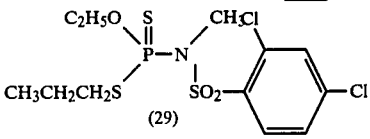 | 100 | 100 | |
| (30) 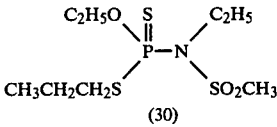 | 100 | 100 | |
| (31) 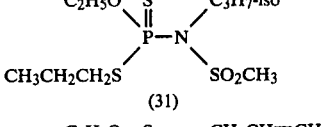 | 100 | 100 | |
| (32) 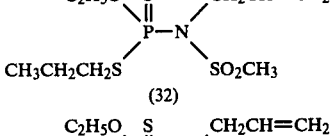 | 100 | 100 | 100 |
| (33) 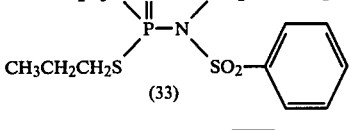 | 100 | 100 | |
| (34) 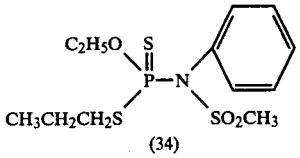 | 100 | 100 | |
| (35) 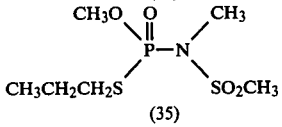 | 100 | 100 | |
| (36) 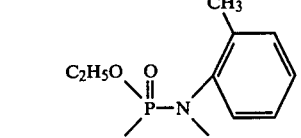 | 100 | 100 | |
| (40) 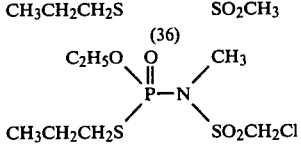 | 100 | 100 | |
| (41) 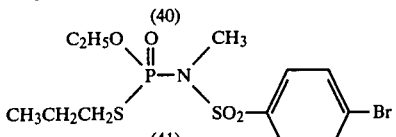 | 100 | 100 | |

TABLE 1-continued

| Compound No. | Kill ratio (%) at a concentration of (ppm) | | |
|---|---|---|---|
| | 1000 | 100 | 10 |
| (A) n-C3H7O, n-C3H7S — P(=O)—NHSO2CH3 | 0 | | |
| (B) n-C3H7O, n-C3H7S — P(=O)—NHSO2—C6H5 | 0 | | |
| (C) (C2H5O)2P(=O)—N(CH3)(SO2—C6H5) | 0 | | |
| (D) (C2H5O)2P(=O)—N(C3H7-iso)(SO2C2H5) | 100 | 0 | |
| (E) (C2H5O)2P(=O)—N(C2H5)(SO2CH3) | 100 | 0 | |

EXAMPLE 4

Test on larvae of *Culex pipiens pallens Coquillett*

100 ml. of an aqueous preparation, at a predetermined concentration, of the active compound was placed in a high-walled Petri dish 9 cm. in diameter. Into the dish were released 25 4th instar larvae of *Culex pipiens pallens Coquillett*, and then the dish was placed in a constant-temperature room at 28° C. Twenty-four hours later the number of dead larvae was determined to calculate the kill ratio. The results are shown in Table 4.

TABLE 4

| Compound No. | Kill ratio (%) at a concentration of active ingredient (ppm) of | | |
|---|---|---|---|
| | 1 | 0.1 | 0.01 |
| (1) C2H5O, CH3CH2CH2S — P(=O)—N(CH3)(SO2—C6H4—Cl) | 100 | | |
| (3) C2H5O, CH3CH2CH2S — P(=O)—N(C6H5)(SO2CH3) | 100 | | |
| (4) C2H5O, CH3CH2CH2S — P(=O)—N(CH3)(SO2C2H5) | 100 | | |
| (5) C2H5O, CH3CH2CH2S — P(=O)—N(CH3)(SO2C4H9-n) | 100 | | |
| (8) C2H5O, CH3CH2CH2S — P(=O)—N(CH3)(SO2—C6H3Cl2 (2,5)) | 100 | | |

TABLE 4-continued
| Compound No. | Kill ratio (%) at a concentration of active ingredient (ppm) of | | |
|---|---|---|---|
| | 1 | 0.1 | 0.01 |
| (9) 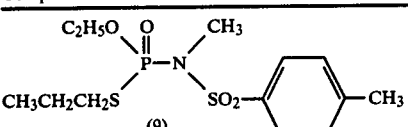 | 100 | | |
| (10) 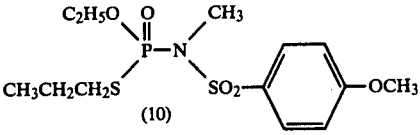 | 100 | | |
| (11) 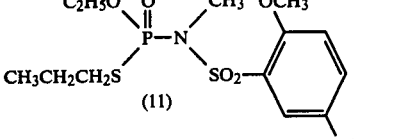 | 100 | 100 | |
| (12) 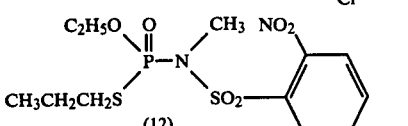 | 100 | 100 | |
| (13) 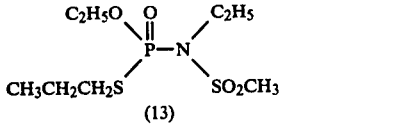 | 100 | | |
| (15) 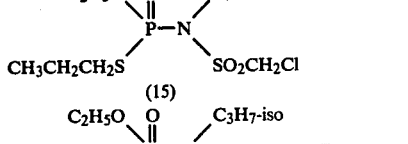 | 100 | | |
| (16) 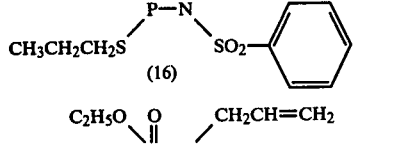 | 100 | | |
| (19) 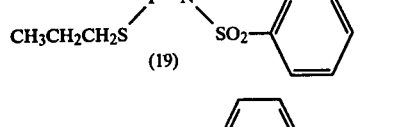 | 100 | | |
| (20) 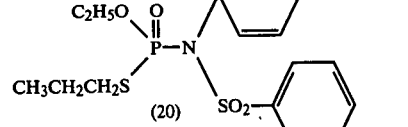 | 100 | | |
| (21) 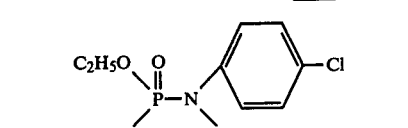 | 100 | | |
| (22) 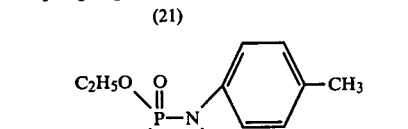 | 100 | | |

TABLE 4-continued
| Compound No. | Kill ratio (%) at a concentration of active ingredient (ppm) of |||
| --- | --- | --- | --- |
| | 1 | 0.1 | 0.01 |
| 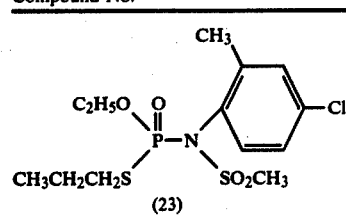 (23) | 100 | | |
| 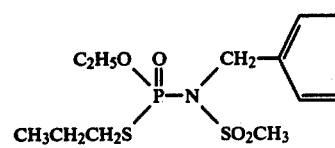 (24) | 100 | | |
| (25) | 100 | | |
| (26) | 100 | | |
| 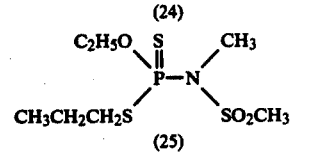 (27) | 100 | 100 | |
| 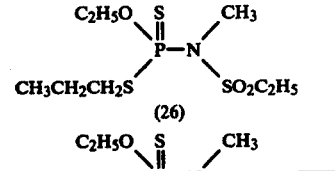 (28) | 100 | 100 | |
| 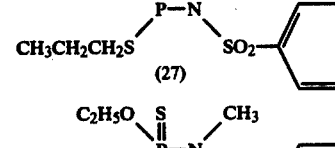 (29) | 100 | 100 | 100 |
| (30) | 100 | | |
| (31) | 100 | | |
| (32) | 100 | | |
| 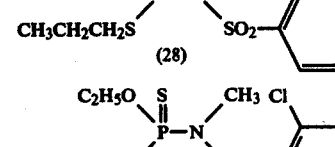 (33) | 100 | | |

TABLE 4-continued

| Compound No. | Kill ratio (%) at a concentration of active ingredient (ppm) of | | |
|---|---|---|---|
| | 1 | 0.1 | 0.01 |
| (34) Compound: C2H5O, CH3CH2CH2S, S=P, N(C6H5)(SO2CH3) | 100 | 100 | |
| (36) Compound: C2H5O, CH3CH2CH2S, O=P, N(2-CH3-C6H4)(SO2CH3) | 100 | | |
| (39) Compound: C2H5O, CH3CH2CH2S, O=P, N(2-CH3-4-Cl-C6H3)(SO2C6H5) | 100 | | |
| (40) Compound: C2H5O, CH3CH2CH2S, O=P, N(CH3)(SO2CH2Cl) | 100 | | |
| (41) Compound: C2H5O, CH3CH2CH2S, O=P, N(CH3)(SO2-C6H4-Br) | 100 | | |
| (42) Compound: C2H5O, CH3CH2CH2S, O=P, N(CH3)(SO2-2,4,5-Cl3-C6H2) | 100 | 100 | 100 |
| (A) n-C3H7O, n-C3H7S, O=P, NHSO2CH3 | 0 | | |
| (B) n-C3H7O, n-C3H7S, O=P, NHSO2C6H5 | 0 | | |
| (C) (C2H5O)2P(=O)-N(CH3)(SO2C6H5) | 0 | | |
| (D) (C2H5O)2P(=O)-N(iso-C3H7)(SO2C2H5) | 0 | | |

TABLE 4-continued

| Compound No. | Kill ratio (%) at a concentration of active ingredient (ppm) of | | |
|---|---|---|---|
| | 1 | 0.1 | 0.01 |
| (C$_2$H$_5$O)$_2$P(O)—N(C$_2$H$_5$)(SO$_2$CH$_3$) (E) | 0 | | |

EXAMPLE 5

Test on *Blattella germanica*

The bottom of a Petri dish 9 cm in diameter was covered with a filter paper, onto which was placed 1 ml of an aqueous preparation, at a predetermined concentration, of the active compound (prepared as in Example 1. 10 imagoes of *Blattella germanica* were placed therein, and the Petri dish was allowed to stand in a constant-temperature room at 28° C. for 24 hours. After 24 hours had elapsed, the number of dead imagoes was determined to calculate the kill ratio. The results are shown in Table 5.

TABLE 5

| Compound No. | Kill ratio (%) at a concentration of active ingredient (ppm) of | |
|---|---|---|
| | 1000 | 100 |
| (1) C$_2$H$_5$O, CH$_3$CH$_2$CH$_2$S—P(O)—N(CH$_3$)(SO$_2$-C$_6$H$_4$-Cl) | 100 | |
| (2) C$_2$H$_5$O, CH$_3$CH$_2$CH$_2$S—P(O)—N(CH$_3$)(SO$_2$CH$_3$) | 100 | |
| (3) C$_2$H$_5$O, CH$_3$CH$_2$CH$_2$S—P(O)—N(C$_6$H$_5$)(SO$_2$CH$_3$) | 100 | |
| (4) C$_2$H$_5$O, CH$_3$CH$_2$CH$_2$S—P(O)—N(CH$_3$)(SO$_2$C$_2$H$_5$) | 100 | |
| (5) C$_2$H$_5$O, CH$_3$CH$_2$CH$_2$S—P(O)—N(CH$_3$)(SO$_2$C$_4$H$_9$-n) | 100 | |
| (6) CH$_3$O, CH$_3$CH$_2$CH$_2$S—P(O)—N(CH$_3$)(SO$_2$-C$_6$H$_5$) | 100 | |
| (8) C$_2$H$_5$O, CH$_3$CH$_2$CH$_2$S—P(O)—N(CH$_3$)(SO$_2$-C$_6$H$_3$Cl$_2$) | 100 | |
| (13) C$_2$H$_5$O, CH$_3$CH$_2$CH$_2$S—P(O)—N(OC$_2$H$_5$)(SO$_2$CH$_3$) | 100 | |
| (15) C$_2$H$_5$O, CH$_3$CH$_2$CH$_2$S—P(O)—N(C$_3$H$_7$-iso)(SO$_2$CH$_2$Cl) | 100 | |
| (17) C$_2$H$_5$O, CH$_3$CH$_2$CH$_2$S—P(O)—N(C$_4$H$_9$-n)(SO$_2$CH$_3$) | 100 | |
| (18) C$_2$H$_5$O, CH$_3$CH$_2$CH$_2$S—P(O)—N(CH$_2$CH=CH$_2$)(SO$_2$CH$_3$) | 100 | |
| (20) C$_2$H$_5$O, CH$_3$CH$_2$CH$_2$S—P(O)—N(C$_6$H$_5$)(SO$_2$-C$_6$H$_5$) | 100 | |
| (23) C$_2$H$_5$O, CH$_3$CH$_2$CH$_2$S—P(O)—N(C$_6$H$_3$(CH$_3$)Cl)(SO$_2$CH$_3$) | 100 | |
| (25) C$_2$H$_5$O, CH$_3$CH$_2$CH$_2$S—P(S)—N(CH$_3$)(SO$_2$CH$_3$) | 100 | 100 |
| (26) C$_2$H$_5$O, CH$_3$CH$_2$CH$_2$S—P(S)—N(CH$_3$)(SO$_2$C$_2$H$_5$) | 100 | 100 |
| (27) C$_2$H$_5$O, CH$_3$CH$_2$CH$_2$S—P(S)—N(CH$_3$)(SO$_2$-C$_6$H$_5$) | 100 | |

TABLE 5-continued

| Compound No. | Kill ratio (%) at a concentration of active ingredient (ppm) of 1000 | 100 |
|---|---|---|
| (28) $C_2H_5O$–P(=S)(–SCH_2CH_2CH_3)–N(CH_3)–C_6H_4–SO_2–(4-Cl) | 100 | |
| (30) $C_2H_5O$–P(=S)(–SCH_2CH_2CH_3)–N(C_2H_5)–SO_2CH_3 | 100 | |
| (31) $C_2H_5O$–P(=S)(–SCH_2CH_2CH_3)–N(iso-C_3H_7)–SO_2CH_3 | 100 | |
| (32) $C_2H_5O$–P(=S)(–SCH_2CH_2CH_3)–N(CH_2CH=CH_2)–SO_2CH_3 | 100 | 100 |
| (33) $C_2H_5O$–P(=S)(–SCH_2CH_2CH_3)–N(CH_2CH=CH_2)–SO_2–C_6H_5 | 100 | |
| (34) $C_2H_5O$–P(=S)(–SCH_2CH_2CH_3)–N(C_6H_5)–SO_2CH_3 | 100 | |
| (36) $C_2H_5O$–P(=O)(–SCH_2CH_2CH_3)–N(CH_3)(–C_6H_5)–SO_2CH_3 | 100 | |
| (39) $C_2H_5O$–P(=O)(–SCH_2CH_2CH_3)–N–(2-CH_3-4-Cl-C_6H_3)–SO–C_6H_5 | 100 | |
| (40) $C_2H_5O$–P(=O)(–SCH_2CH_2CH_3)–N(CH_3)–SO_2CH_2Cl | 100 | |
| (41) $C_2H_5O$–P(=O)(–SCH_2CH_2CH_3)–N(CH_3)–SO_2–C_6H_4–(4-Br) | 100 | |
| (A) n-C_3H_7O–P(=O)(–S-n-C_3H_7)–NHSO_2CH_3 | 0 | |
| (B) n-C_3H_7O–P(=O)(–S-n-C_3H_7)–NHSO_2–C_6H_5 | 0 | |
| (C) $(C_2H_5O)_2$P(=O)–N(CH_3)–C_6H_4–SO_2 | 0 | |
| (D) $(C_2H_5O)_2$P(=O)–N(iso-C_3H_7)–SO_2C_2H_5 | 0 | |
| (E) $(C_2H_5O)_2$P(=O)–N(C_2H_5)–SO_2CH_3 | 0 | |

EXAMPLE 6

Test on *Musca domestica vicina*

A filter paper was laid on the bottom of a Petri dish 9 cm in diameter, and 1 ml of an aqueous preparation, at a predetermined concentration, of the active compound (prepared as in Example 1) was put into the dish. 10 female imagos of *Musca domestica vicina* were introduced therein. Then, the dish was placed in a constant-temperature room at 28° C., and 24 hours later, the number of killed imagos was determined in order to calculate the kill ratio. The results are shown in Table 6.

TABLE 6

| Compound No. | Kill ratio (%) at a concentration of active ingredient (ppm) of 1000 | 100 |
|---|---|---|
| (1) $C_2H_5O$–P(=O)(–SCH_2CH_2CH_3)–N(CH_3)–C_6H_4–SO_2–(4-Cl) | 100 | |
| (2) $C_2H_5O$–P(=O)(–SCH_2CH_2CH_3)–N(CH_3)–SO_2CH_3 | 100 | 100 |
| (3) $C_2H_5O$–P(=O)(–SCH_2CH_2CH_3)–N(C_6H_5)–SO_2CH_3 | 100 | 100 |
| (4) $C_2H_5O$–P(=O)(–SCH_2CH_2CH_3)–N(CH_3)–SO_2C_2H_5 | 100 | |
| (5) $C_2H_5O$–P(=O)(–SCH_2CH_2CH_3)–N(CH_3)–SO_2C_4H_9-n | 100 | 100 |

TABLE 6-continued

| Compound No. | Kill ratio (%) at a concentration of active ingredient (ppm) of 1000 | 100 |
|---|---|---|
| (6) CH₃O, O, CH₃; CH₃CH₂CH₂S–P(=O)–N–SO₂–C₆H₅ | 100 | |
| (7) C₂H₅O, O, CH₃; CH₃CH₂CH₂S–P(=O)–N–SO₂–C₆H₅ | 100 | |
| (8) C₂H₅O, O, CH₃; CH₃CH₂CH₂S–P(=O)–N–SO–C₆H₃Cl₂ | 100 | 100 |
| (10) C₂H₅O, O, CH₃; CH₃CH₂CH₂S–P(=O)–N–SO₂–C₆H₄OCH₃ | 100 | |
| (12) C₂H₅O, O, CH₃; CH₃CH₂CH₂S–P(=O)–N–SO₂–C₆H₄NO₂ | 100 | |
| (13) C₂H₅O, O, C₂H₅; CH₃CH₂CH₂S–P(=O)–N–SO₂CH₃ | 100 | 100 |
| (14) C₂H₅O, O, C₃H₇-iso; CH₃CH₂CH₂S–P(=O)–N–SO₂CH₃ | 100 | |
| (15) C₂H₅O, O, C₃H₇-iso; CH₃CH₂CH₂S–P(=O)–N–SO₂CH₂Cl | 100 | |
| (16) C₂H₅O, O, C₃H₇-iso; CH₃CH₂CH₂S–P(=O)–N–SO₂–C₆H₅ | 100 | |
| (17) C₂H₅O, O, C₄H₉-n; CH₃CH₂CH₂S–P(=O)–N–SO₂CH₃ | 100 | 100 |
| (18) C₂H₅O, O, CH₂CH=CH₂; CH₃CH₂CH₂S–P(=O)–N–SO₂CH₃ | 100 | 100 |
| (19) C₂H₅O, O, CH₂CH=CH₂; CH₃CH₂CH₂S–P(=O)–N–SO₂–C₆H₅ | 100 | 100 |
| (20) C₂H₅O, O, CH₂–C₆H₅; CH₃CH₂CH₂S–P(=O)–N–SO₂–C₆H₅ | 100 | |
| (21) C₂H₅O, O, C₆H₄Cl; CH₃CH₂CH₂S–P(=O)–N–SO₂CH₃ | 100 | 100 |
| (22) C₂H₅O, O, C₆H₄CH₃; CH₃CH₂CH₂S–P(=O)–N–SO₂CH₃ | 100 | |
| (23) C₂H₅O, O, C₆H₃(CH₃)(Cl); CH₃CH₂CH₂S–P(=O)–N–SO₂CH₃ | 100 | |
| (24) C₂H₅O, O, CH₂–C₆H₅; CH₃CH₂CH₂S–P(=O)–N–SO₂CH₃ | 100 | 100 |
| (25) C₂H₅O, S, CH₃; CH₃CH₂CH₂S–P(=S)–N–SO₂CH₃ | 100 | 100 |
| (26) C₂H₅O, S, CH₃; CH₃CH₂CH₂S–P(=S)–N–SO₂C₂H₅ | 100 | |
| (27) C₂H₅O, S, CH₃; CH₃CH₂CH₂S–P(=S)–N–SO₂–C₆H₅ | 100 | |
| (28) C₂H₅O, S, CH₃; CH₃CH₂CH₂S–P(=S)–N–SO₂–C₆H₄Cl | 100 | 100 |
| (29) C₂H₅O, S, CH₃; CH₃CH₂CH₂S–P(=S)–N–SO₂–C₆H₃Cl₂ | 100 | 100 |
| (30) C₂H₅O, S, C₂H₅; CH₃CH₂CH₂S–P(=S)–N–SO₂CH₃ | 100 | 100 |
| (31) C₂H₅O, S, C₃H₇-iso; CH₃CH₂CH₂S–P(=S)–N–SO₂CH₃ | 100 | |
| (32) C₂H₅O, S, CH₂CH=CH₂; CH₃CH₂CH₂S–P(=S)–N–SO₂CH₃ | 100 | 100 |

TABLE 6-continued

| Compound No. | Kill ratio (%) at a concentration of active ingredient (ppm) of | |
|---|---|---|
| | 1000 | 100 |
| (33) $C_2H_5O$, S, $CH_3CH_2CH_2S$, P—N, $CH_2CH=CH_2$, $SO_2$—Ph | 100 | 100 |
| (34) $C_2H_5O$, S, $CH_3CH_2CH_2S$, P—N, Ph, $SO_2CH_3$ | 100 | |
| (35) $CH_3O$, O, $CH_3CH_2CH_2S$, P—N, $CH_3$, $SO_2CH_3$ | 100 | |
| (36) $C_2H_5O$, O, $CH_3CH_2CH_2S$, P—N, $CH_3$-Ph, $SO_2CH_3$ | 100 | |
| (40) $C_2H_5O$, O, $CH_3CH_2CH_2S$, P—N, $CH_3$, $SO_2CH_2Cl$ | 100 | |
| (41) $C_2H_5O$, O, $CH_3CH_2CH_2S$, P—N, $CH_3$, $SO_2$—Ph—Br | 100 | |
| (A) $n$-$C_3H_7O$, O, $n$-$C_3H_7S$, P—$NHSO_2CH_3$ | 0 | |
| (B) $n$-$C_3H_7O$, O, $n$-$C_3H_7S$, P—$NHSO_2$—Ph | 0 | |
| (C) $(C_2H_5O)_2$P(O)—N, $CH_3$, $SO_2$—Ph | 0 | |

EXAMPLE 7

Test on the two-spotted spider mite, *Tetranychus telarius* (spray test)

The leaves of kidney bean plants in the two-leaf stage were infested with 50 to 100 imagos of *Tetranychus telarius* (a resistant strain with respect to organophosphorus compounds). The kidney bean plants were cultivated in pots each 9 cm in diameter. Two days after the infestation, an aqueous preparation, at a predetermined concentration, of the active compound (formulated as in Example 1) was sprayed over the leaves at a rate of 20 ml per pot. Then, the pots were put in a greenhouse. 10 days later, the acaricidal effect was evaluated and expressed on the following scale:

3—0% survival of the spider mites
2—not more than 5% survival based on an untreated control
1—6–50% survival based on an untreated control
0—more than 51% survival based on an untreated control The results are shown in Table 7.

TABLE 7

| Compound No. | Kill ratio (%) in a concentration of active ingredient (ppm) of | | | | |
|---|---|---|---|---|---|
| | 1000 | 300 | 100 | 50 | 10 |
| (1) $C_2H_5O$, O, $CH_3CH_2CH_2S$, P—N, $CH_3$, $SO_2$—Ph—Cl | 3 | 3 | 3 | 3 | |
| (2) $C_2H_5O$, O, $CH_3CH_2CH_2S$, P—N, $CH_3$, $SO_2CH_3$ | 3 | 3 | 3 | 3 | 2 |
| (3) $C_2H_5O$, O, $CH_3CH_2CH_2S$, P—N, Ph, $SO_2CH_3$ | 3 | 3 | 3 | 3 | |
| (4) $C_2H_5O$, O, $CH_3CH_2CH_2S$, P—N, $CH_3$, $SO_2C_2H_5$ | 3 | 3 | 3 | | |
| (5) $C_2H_5O$, O, $CH_3CH_2CH_2S$, P—N, $CH_3$, $SO_2C_4H_9$-n | 3 | 3 | 2 | | |
| (6) $CH_3O$, O, $CH_3CH_2CH_2S$, P—N, $CH_3$, $SO_2$—Ph | 3 | 3 | 3 | 3 | |
| (7) $C_2H_5O$, O, $CH_3CH_2CH_2S$, P—N, $CH_3$, $SO_2$—Ph | 3 | 3 | 3 | 3 | |
| (8) $C_2H_5O$, O, $CH_3CH_2CH_2S$, P—N, $CH_3$, $SO_2$—Ph(Cl)(Cl) | 3 | 3 | 3 | 3 | 3 |
| (9) $C_2H_5O$, O, $CH_3CH_2CH_2S$, P—N, $CH_3$, $SO_2$—Ph—$CH_3$ | 3 | 3 | | | |
| (10) $C_2H_5O$, O, $CH_3CH_2CH_2S$, P—N, $CH_3$, $SO_2$—Ph—$OCH_3$ | 3 | 3 | | | |
| (11) $C_2H_5O$, O, $CH_3CH_2CH_2S$, P—N, $CH_3$, $SO_2$—Ph($OCH_3$)(Cl) | 3 | 3 | 3 | 2 | |
| (12) $C_2H_5O$, O, $CH_3CH_2CH_2S$, P—N, $CH_3$, $SO_2$—Ph—$NO_2$ | 3 | 3 | 3 | 3 | 3 |
| (13) $C_2H_5O$, O, $CH_3CH_2CH_2S$, P—N, $C_2H_5$, $SO_2CH_3$ | 3 | 3 | 2 | | |

TABLE 7-continued

| Compound No. | Kill ratio (%) in a concentration of active ingredient (ppm) of | | | | |
|---|---|---|---|---|---|
| | 1000 | 300 | 100 | 50 | 10 |
| (14) C2H5O, O, CH3CH2CH2S, P-N, C3H7-iso, SO2CH3 | 3 | 3 | 3 | 3 | |
| (15) C2H5O, O, CH3CH2CH2S, P-N, i-C3H7, SO2CH2Cl | 3 | 3 | 3 | 3 | |
| (16) C2H5O, O, CH3CH2CH2S, P-N, C3H7-iso, SO2-Ph | 3 | 3 | 3 | | |
| (17) C2H5O, O, CH3CH2CH2S, P-N, C4H9-n, SO2CH3 | 3 | 3 | 3 | 3 | |
| (18) C2H5O, O, CH3CH2CH2S, P-N, CH2CH=CH2, SO2CH3 | 3 | 3 | 3 | | |
| (19) C2H5O, O, CH3CH2CH2S, P-N, CH2CH=CH2, SO2-Ph | 3 | 3 | 3 | | |
| (20) C2H5O, O, CH3CH2CH2S, P-N, Ph, SO2-Ph | 3 | 3 | 3 | 3 | |
| (21) C2H5O, O, CH3CH2CH2S, P-N, Ph-Cl, SO2CH3 | 3 | 3 | 3 | 3 | |
| (22) C2H5O, O, CH3CH2CH2S, P-N, Ph-CH3, SO2CH3 | 3 | 3 | 3 | 3 | 3 |
| (23) C2H5O, O, CH3CH2CH2S, P-N, CH3-Ph-Cl, SO2CH3 | 3 | 3 | 3 | 3 | 3 |
| (24) C2H5O, O, CH3CH2CH2S, P-N, CH2Ph, SO2CH3 | 3 | 3 | 3 | 3 | 2 |
| (25) C2H5O, S, CH3CH2CH2S, P-N, CH3, SO2CH3 | 3 | 3 | 3 | | |
| (26) C2H5O, S, CH3CH2CH2S, P-N, CH3, SO2C2H5 | 3 | 3 | 3 | | |
| (27) C2H5O, S, CH3CH2CH2S, P-N, CH3, SO2-Ph | 3 | 3 | 2 | | |
| (28) C2H5O, S, CH3CH2CH2S, P-N, CH3, SO2-Ph-Cl | 3 | 3 | | | |
| (29) C2H5O, S, CH3CH2CH2S, P-N, CH3, SO2-Ph(Cl)2 | 3 | 3 | | | |
| (30) C2H5O, S, CH3CH2CH2S, P-N, C2H5, SO2CH3 | 3 | 3 | 3 | 2 | |
| (31) C2H5O, S, CH3CH2CH2S, P-N, C3H7-iso, SO2CH3 | 3 | 3 | 3 | | |
| (32) C2H5O, S, CH3CH2CH2S, P-N, CH2CH=CH2, SO2CH3 | 3 | 3 | 2 | | |
| (33) C2H5O, S, CH3CH2CH2S, P-N, CH2CH=CH2, SO2-Ph | 3 | 3 | | | |
| (34) C2H5O, S, CH3CH2CH2S, P-N, Ph, SO2CH3 | 3 | 3 | | | |
| (35) CH3O, O, CH3CH2CH2S, P-N, CH3, SO2CH3 | 3 | 3 | 3 | | |
| (36) C2H5O, O, CH3CH2CH2S, P-N, CH2-Ph-CH3, SO2CH3 | 3 | 3 | 3 | | |
| (37) C2H5O, O, CH3CH2CH2S, P-N, CH3-Ph-CH3, SO2CH3 | 3 | 3 | 3 | | |
| (38) C2H5O, O, CH3CH2CH2S, P-N, Ph(Cl)2, SO2CH3 | 3 | 3 | 3 | | |
| (39) C2H5O, O, CH3CH2CH2S, P-N, CH3-Ph-Cl, SO-Ph | 3 | 3 | 3 | | |
| (40) C2H5O, O, CH3CH2CH2S, P-N, CH3, SO2CH2Cl | 3 | 3 | 3 | | |

TABLE 7-continued

| Compound No. | Kill ratio (%) in a concentration of active ingredient (ppm) of | | | | |
|---|---|---|---|---|---|
| | 1000 | 300 | 100 | 50 | 10 |
| (41) $C_2H_5O$, $CH_3CH_2CH_2S$ — P(=O) — N(CH$_3$)SO$_2$—C$_6$H$_4$—Br | 3 | 3 | 3 | | |
| (42) $C_2H_5O$, $CH_3CH_2CH_2S$ — P(=O) — N(CH$_3$)SO$_2$—C$_6$H$_3$Cl$_2$ | 3 | 3 | 3 | | |
| (A) n-$C_3H_7O$, n-$C_3H_7S$ — P(=O) — NHSO$_2$CH$_3$ | 0 | | | | |
| (B) n-$C_3H_7O$, n-$C_3H_7S$ — P(=O) — NHSO$_2$—C$_6$H$_5$ | 0 | | | | |
| (C) $(C_2H_5O)_2$P(=O) — N(CH$_3$)SO$_2$—C$_6$H$_5$ | 0 | | | | |
| (D) $(C_2H_5O)_2$P(=O) — N(C$_3$H$_7$-iso)SO$_2$C$_2$H$_5$ | 0 | | | | |
| (E) $(C_2H_5O)_2$P(=O) — N(C$_2$H$_5$)SO$_2$CH$_3$ | 0 | | | | |

EXAMPLE 8

Test on the two-spotted spider mite, *Tetranychus telarius* (irrigation test)

The leaves of kidney bean plants in the two-leaf stage were infested with 50 to 100 imagos of *Tetranychus telarius* (a resistant strain with respect to organophosphorus compounds).

Two days later, an aqueous preparation, at a predetermined concentration, of the active compound (formulated as in Example 1) was fed, by irrigation, to the roots of the kidney bean plants at a rate of 20 ml per pot. Then, the pots were placed in a greenhouse, and 10 days later, the acaricidal effect was evaluated and expressed on the following scale:

3—0% survival of the spider mites
2—not more than 5% survival based on an untreated control
1—6–50% survival based on an untreated control
0—more than 51% survival based on an untreated control The results are shown in Table 8.

TABLE 8

| Compound No. | Kill ratio (%) in a concentration of active ingredient (ppm) of | | | | |
|---|---|---|---|---|---|
| | 1000 | 300 | 100 | 50 | 10 |
| (1) $C_2H_5O$, $CH_3CH_2CH_2S$ — P(=O) — N(CH$_3$)SO$_2$—C$_6$H$_4$—Cl | 3 | | | | |
| (2) $C_2H_5O$, $CH_3CH_2CH_2S$ — P(=O) — N(CH$_3$)SO$_2$CH$_3$ | 3 | 3 | 3 | 3 | 3 |
| (3) $C_2H_5O$, $CH_3CH_2CH_2S$ — P(=O) — N(C$_6$H$_5$)SO$_2$CH$_3$ | 3 | 3 | 3 | | |
| (4) $C_2H_5O$, $CH_3CH_2CH_2S$ — P(=O) — N(CH$_3$)SO$_2$C$_2$H$_5$ | 3 | 3 | 3 | | |
| (5) $C_2H_5O$, $CH_3CH_2CH_2S$ — P(=O) — N(CH$_3$)SO$_2$C$_4$H$_9$-n | 3 | 3 | | | |
| (6) $CH_3O$, $CH_3CH_2CH_2S$ — P(=O) — N(CH$_3$)SO$_2$—C$_6$H$_5$ | 3 | 2 | | | |
| (7) $C_2H_5O$, $CH_3CH_2CH_2S$ — P(=O) — N(CH$_3$)SO$_2$—C$_6$H$_5$ | 3 | | | | |

TABLE 8-continued

| Compound No. | Kill ratio (%) in a concentration of active ingredient (ppm) of | | | | |
|---|---|---|---|---|---|
| | 1000 | 300 | 100 | 50 | 10 |
| (8) C₂H₅O-P(=O)(SCH₂CH₂CH₃)-N(CH₃)-SO₂-(2,5-Cl₂C₆H₃) | 3 | | | | |
| (13) C₂H₅O-P(=O)(SCH₂CH₂CH₃)-N(C₂H₅)-SO₂CH₃ | 3 | 3 | 3 | | |
| (14) C₂H₅O-P(=O)(SCH₂CH₂CH₃)-N(C₃H₇-iso)-SO₂CH₃ | 3 | 3 | 3 | | |
| (15) C₂H₅O-P(=O)(SCH₂CH₂CH₃)-N(C₃H₇-iso)-SO₂CH₂Cl | 3 | 3 | 2 | | |
| (17) C₂H₅O-P(=O)(SCH₂CH₂CH₃)-N(C₄H₉-n)-SO₂CH₃ | 3 | 3 | 3 | | |
| (18) C₂H₅O-P(=O)(SCH₂CH₂CH₃)-N(CH₂CH=CH₂)-SO₂CH₃ | 3 | 3 | 3 | | |
| (21) C₂H₅O-P(=O)(SCH₂CH₂CH₃)-N(C₆H₄-Cl)-SO₂CH₃ | 3 | 3 | | | |
| (22) C₂H₅O-P(=O)(SCH₂CH₂CH₃)-N(C₆H₄-CH₃)-SO₂CH₃ | 3 | 3 | | | |
| (23) C₂H₅O-P(=O)(SCH₂CH₂CH₃)-N(2-CH₃-4-Cl-C₆H₃)-SO₂CH₃ | 3 | 3 | | | |
| (24) C₂H₅O-P(=O)(SCH₂CH₂CH₃)-N(CH₂C₆H₅)-SO₂CH₃ | 3 | 2 | | | |
| (25) C₂H₅O-P(=S)(SCH₂CH₂CH₃)-N(CH₃)-SO₂CH₃ | 3 | 3 | 3 | | |
| (26) C₂H₅O-P(=S)(SCH₂CH₂CH₃)-N(CH₃)-SO₂C₂H₅ | 3 | 3 | 3 | | |
| (30) C₂H₅O-P(=S)(SCH₂CH₂CH₃)-N(C₂H₅)-SO₂CH₃ | 3 | | | | |
| (31) C₂H₅O-P(=S)(SCH₂CH₂CH₃)-N(C₃H₇-iso)-SO₂CH₃ | 3 | | | | |

TABLE 8-continued

| Compound No. | Kill ratio (%) in a concentration of active ingredient (ppm) of | | | | |
|---|---|---|---|---|---|
| | 1000 | 300 | 100 | 50 | 10 |
| (32) $C_2H_5O$-P(=S)(-SCH$_2$CH$_2$CH$_3$)-N(CH$_2$CH=CH$_2$)(SO$_2$CH$_3$) | 3 | | | | |
| (35) $CH_3O$-P(=O)(-SCH$_2$CH$_2$CH$_3$)-N(CH$_3$)(SO$_2$CH$_3$) | 3 | 3 | 3 | | |
| (36) $C_2H_5O$-P(=O)(-SCH$_2$CH$_2$CH$_3$)-N(o-tolyl)(SO$_2$CH$_3$) | 3 | | | | |
| (40) $C_2H_5O$-P(=O)(-SCH$_2$CH$_2$CH$_3$)-N(CH$_3$)(SO$_2$CH$_2$Cl) | 3 | 3 | 3 | | |
| (A) n-C$_3$H$_7$O-P(=O)(-S-n-C$_3$H$_7$)-NHSO$_2$CH$_3$ | 0 | | | | |
| (B) n-C$_3$H$_7$O-P(=O)(-S-n-C$_3$H$_7$)-NHSO$_2$-C$_6$H$_5$ | 0 | | | | |
| (C) (C$_2$H$_5$O)$_2$P(=O)-N(CH$_3$)(SO$_2$-C$_6$H$_5$) | 0 | | | | |
| (D) (C$_2$H$_5$O)$_2$P(=O)-N(C$_3$H$_7$-iso)(SO$_2$C$_2$H$_5$) | 0 | | | | |
| (E) (C$_2$H$_5$O)$_2$P(=O)-N(C$_2$H$_5$)(SO$_2$CH$_3$) | 0 | | | | |

EXAMPLE 9

Test on *Meloidogyne incognita acrita*

An active-compound preparation was prepared by pulverizing and mixing 2 parts by weight of the active compound and 98 parts by weight of talc.

The active compound processed as above was added to soil infested by *Meloidogyne incognita acrita* In such amounts as to give a concentration of 50 ppm, 25 ppm, 10 ppm and 5 ppm, respectively. The mixture was stirred and mixed uniformly and then charged into pots each of 0.0002 are. In the treated soil were sown about 20 seeds of tomato (variety: KURIHARA) per pot. The tomato seeds were cultivated in a greenhouse. Four weeks later, the grown roots were withdrawn without damaging them, and the degree of injury of 10 roots out of them was evaluated based on the following ratings to determine a root-knot index:

Degree of Injury

0—no root-knot formation (perfect control)
1—slight root-knot formation
3—much root-knot formation
4—most root-knot formation (corresponding to non-treatment)

$$\text{Root-knot index} = \frac{(\text{rating} \times \text{number of roots})}{\left(\begin{array}{c}\text{total number of}\\\text{examined roots}\end{array}\right) \times 4} \times 100$$

From above, the following control effect was obtained:

$$\text{Control effect} = \frac{\left(\begin{array}{c}\text{root-knot index}\\\text{of untreated plot}\end{array}\right) - \left(\begin{array}{c}\text{root-knot index}\\\text{of treated plot}\end{array}\right)}{\text{root-knot index of untreated plot}} \times 100$$

A control effect of 100% means perfect control. The results are shown in Table 9.

TABLE 9

| Compound No. | 50 | 25 | 10 | 5 |
|---|---|---|---|---|
| (1) $C_2H_5O$, $CH_3CH_2CH_2S$ — P(=O) — N(CH_3)(SO_2-C_6H_4-Cl) | 100 | 100 | | |
| (2) $C_2H_5O$, $CH_3CH_2CH_2S$ — P(=O) — N(CH_3)(SO_2CH_3) | 100 | 100 | 100 | 100 |
| (3) $C_2H_5O$, $CH_3CH_2CH_2S$ — P(=O) — N(C_6H_5)(SO_2CH_3) | 100 | 100 | 100 | 100 |
| (4) $C_2H_5O$, $CH_3CH_2CH_2S$ — P(=O) — N(CH_3)(SO_2C_2H_5) | 100 | 100 | 100 | 100 |
| (5) $C_2H_5O$, $CH_3CH_2CH_2S$ — P(=O) — N(CH_3)(SO_2C_4H_9\text{-}n) | 100 | 100 | 100 | 100 |
| (6) $CH_3O$, $CH_3CH_2CH_2S$ — P(=O) — N(CH_3)(SO_2-C_6H_5) | 100 | 88.0 | | |
| (7) $C_2H_5O$, $CH_3CH_2CH_2S$ — P(=O) — N(CH_3)(SO_2-C_6H_5) | 100 | 100 | 100 | 100 |
| (8) $C_2H_5O$, $CH_3CH_2CH_2S$ — P(=O) — N(CH_3)(SO_2-C_6H_3Cl_2) | 100 | 100 | | |
| (9) $C_2H_5O$, $CH_3CH_2CH_2S$ — P(=O) — N(CH_3)(SO_2-C_6H_4-CH_3) | 100 | | | |
| (10) $C_2H_5O$, $CH_3CH_2CH_2S$ — P(=O) — N(CH_3)(SO_2-C_6H_4-OCH_3) | 100 | | | |
| (11) $C_2H_5O$, $CH_3CH_2CH_2S$ — P(=O) — N(CH_3)(SO_2-C_6H_3(OCH_3)(Cl)) | 100 | 100 | | |
| (12) $C_2H_5O$, $CH_3CH_2CH_2S$ — P(=O) — N(CH_3)(SO_2-C_6H_4-NO_2) | 100 | 100 | | |
| (13) $C_2H_5O$, $CH_3CH_2CH_2S$ — P(=O) — N(C_2H_5)(SO_2CH_3) | 100 | 100 | 100 | 100 |
| (14) $C_2H_5O$, $CH_3CH_2CH_2S$ — P(=O) — N(C_3H_7\text{-}iso)(SO_2CH_3) | 100 | 100 | | |

TABLE 9-continued

| Compound No. | Structure | 50 | 25 | 10 | 5 |
|---|---|---|---|---|---|
| (15) | $C_2H_5O$, $CH_3CH_2CH_2S$ — P(=O) — N(i-$C_3H_7$-iso)($SO_2CH_2Cl$) | 100 | 100 | 93.2 | |
| (16) | $C_2H_5O$, $CH_3CH_2CH_2S$ — P(=O) — N($C_3H_7$-iso)($SO_2$-phenyl) | 100 | | | |
| (17) | $C_2H_5O$, $CH_3CH_2CH_2S$ — P(=O) — N($C_4H_9$-n)($SO_2CH_3$) | 100 | 100 | 100 | |
| (18) | $C_2H_5O$, $CH_3CH_2CH_2S$ — P(=O) — N($CH_2CH=CH_2$)($SO_2CH_3$) | 100 | 100 | 100 | 100 |
| (19) | $C_2H_5O$, $CH_3CH_2CH_2S$ — P(=O) — N($CH_2CH=CH_2$)($SO_2$-phenyl) | 100 | 95.0 | | |
| (20) | $C_2H_5O$, $CH_3CH_2CH_2S$ — P(=O) — N(phenyl)($SO_2$-phenyl) | 100 | 100 | 100 | 82.5 |
| (21) | $C_2H_5O$, $CH_3CH_2CH_2S$ — P(=O) — N(4-Cl-phenyl)($SO_2CH_3$) | 100 | 100 | 100 | 88.3 |
| (22) | $C_2H_5O$, $CH_3CH_2CH_2S$ — P(=O) — N(4-$CH_3$-phenyl)($SO_2CH_3$) | 100 | 100 | | |
| (23) | $C_2H_5O$, $CH_3CH_2CH_2S$ — P(=O) — N(2-$CH_3$-4-Cl-phenyl)($SO_2CH_3$) | 100 | 100 | 100 | 83.6 |
| (24) | $C_2H_5O$, $CH_3CH_2CH_2S$ — P(=O) — N($CH_2$-phenyl)($SO_2CH_3$) | 100 | 100 | 100 | |
| (25) | $C_2H_5O$, $CH_3CH_2CH_2S$ — P(=S) — N($CH_3$)($SO_2CH_3$) | 100 | 100 | 92.9 | |
| (26) | $C_2H_5O$, $CH_3CH_2CH_2S$ — P(=S) — N($CH_3$)($SO_2C_2H_5$) | 100 | 100 | | |
| (27) | $C_2H_5O$, $CH_3CH_2CH_2S$ — P(=S) — N($CH_3$)($SO_2$-phenyl) | 100 | | | |

TABLE 9-continued

| Compound No. | Control effect (%) at a concentration of active ingredient (ppm) of | | | |
|---|---|---|---|---|
| | 50 | 25 | 10 | 5 |
| (28) $C_2H_5O$-P(=S)(SCH_2CH_2CH_3)-N(CH_3)-SO_2-C_6H_4-Cl | 100 | | | |
| (29) $C_2H_5O$-P(=S)(SCH_2CH_2CH_3)-N(CH_3)-SO_2-C_6H_3Cl_2 | 100 | | | |
| (30) $C_2H_5O$-P(=S)(SCH_2CH_2CH_3)-N(C_2H_5)-SO_2CH_3 | 100 | 100 | 95.0 | |
| (31) $C_2H_5O$-P(=S)(SCH_2CH_2CH_3)-N(C_3H_7\text{-iso})-SO_2CH_3 | 100 | 100 | | |
| (32) $C_2H_5O$-P(=S)(SCH_2CH_2CH_3)-N(CH_2CH=CH_2)-SO_2CH_3 | 100 | 89.1 | | |
| (33) $C_2H_5O$-P(=S)(SCH_2CH_2CH_3)-N(CH_2CH=CH_2)-SO_2-C_6H_5 | 100 | | | |
| (34) $C_2H_5O$-P(=S)(SCH_2CH_2CH_3)-N(C_6H_5)-SO_2CH_3 | 100 | 97.5 | | |
| (35) $CH_3O$-P(=O)(SCH_2CH_2CH_3)-N(CH_3)-SO_2CH_3 | 100 | 100 | 100 | 100 |
| (36) $C_2H_5O$-P(=O)(SCH_2CH_2CH_3)-N(2-CH_3-C_6H_4)-SO_2CH_3 | 100 | 100 | 100 | 100 |
| (37) $C_2H_5O$-P(=O)(SCH_2CH_2CH_3)-N(2,4-(CH_3)_2-C_6H_3)-SO_2CH_3 | 100 | 74.7 | | |
| (38) $C_2H_5O$-P(=O)(SCH_2CH_2CH_3)-N(2,4-Cl_2-C_6H_3)-SO_2CH_3 | 100 | 70.7 | | |
| (39) $C_2H_5O$-P(=O)(SCH_2CH_2CH_3)-N(2-CH_3-4-Cl-C_6H_3)-SO-C_6H_5 | 100 | 100 | 70.0 | |
| (40) $C_2H_5O$-P(=O)(SCH_2CH_2CH_3)-N(CH_3)-SO_2CH_2Cl | 100 | 100 | 100 | 100 |

TABLE 9-continued

| Compound No. | Control effect (%) at a concentration of active ingredient (ppm) of | | | |
|---|---|---|---|---|
| | 50 | 25 | 10 | 5 |
| (41) C₂H₅O–P(=O)(–SCH₂CH₂CH₃)–N(CH₃)–SO₂–C₆H₄–Br | 100 | 100 | 64.3 | |
| (42) C₂H₅O–P(=O)(–SCH₂CH₂CH₃)–N(CH₃)–SO₂–C₆H₂Cl₃ | 100 | 100 | 74.0 | |
| (A) n-C₃H₇O–P(=O)(–S-n-C₃H₇)–NHSO₂CH₃ | 0 | | | |
| (B) n-C₃H₇O–P(=O)(–S-n-C₃H₇)–NHSO₂–C₆H₅ | 0 | | | |
| (C) (C₂H₅O)₂P(=O)–N(CH₃)–SO₂–C₆H₅ | 0 | | | |
| (D) (C₂H₅O)₂P(=O)–N(C₃H₇-iso)–SO₂C₂H₅ | 22.3 | | | |
| (E) (C₂H₅O)₂P(=O)–N(C₂H₅)–SO₂CH₃ | 22.3 | | | |

The following preparative Examples illustrate the process for preparing the compounds of the present invention:

EXAMPLE 10

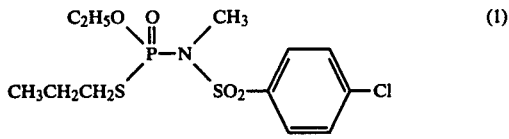
(1)

37 g of potassium O-ethyl-N-methyl-N-4-chlorobenzenesulfonylphosphoramidothioate was dissolved in 150 ml of methyl ethyl ketone, and 14 g of n-propyl bromide was added. The mixture was heated at 60°–70° C. for 3 hours to complete the reaction. After distilling off the methyl ethyl ketone, toluene was added to the residue, and the mixture was washed with water, with 1% aqueous sodium hydroxide and again with water. After distilling off the toluene under reduced pressure, 31 g of O-ethyl-S-n-propyl-N-methyl-N-4-chlorobenzenesulfonylphosphoramidothiolate was obtained as a colorless oil ($n_D^{20} = 1.5335$).

EXAMPLE 11

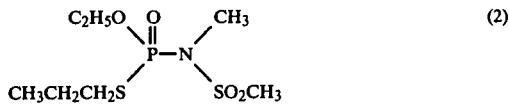
(2)

5.6 g of potassium hydroxide was dissolved in 100 ml of ethanol, and the solution was saturated with gaseous hydrogen sulfide at room temperature to form an ethanol solution of potassium hydrosulfide. 26 g of O,O-diethyl-N-methyl-N-methane sulfonylphosphoramidothioate was added to this solution, and the mixture was stirred at 75°–80° C. for 4 hours. The internal temperature was cooled to about 40° C., and then 14 g of n-propyl bromide was added, followed by stirring at 65° C. for 3 hours to complete the reaction.

The volatile components were removed from the reaction mixture under reduced pressure, toluene was added to the residue, and the mixture was washed with water, with 1% aqueous sodium hydroxide and again with water. After drying the mixture over anhydrous sodium sulfate, toluene was removed to obtain 22 g of O-ethyl-S-n-propyl-N-methyl-N-methanesulfonylphosphoramidothiolate as a colorless oil ($n_D^{20} = 1.5020$).

EXAMPLE 12

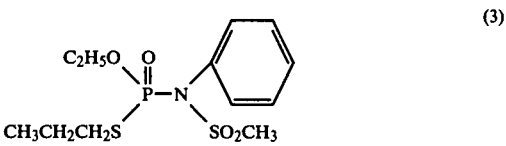
(3)

21 g of sodium methanesulfonanilide was suspended in 150 ml of toluene, and 20 g of O-ethyl-S-n-propylthiophosphoryl chloride was added. The mixture was heated at 80°–90° C. for 3 to 4 hours to complete the reaction. After the reaction had ceased, the reaction mixture was cooled to room temperature and washed with water, with a 1% aqueous solution of sodium hydroxide, and again with water. The mixture was then dried over anhydrous sodium sulfate.

Toluene was distilled from the dried reaction mixture under reduced pressure to obtain 25 g of O-ethyl-S-n-propyl-N-phenyl-N-methanesulfonylphosphoramidothiolate as a colorless oil ($n_D^{20}=1.5400$).

The following compounds were prepared by procedures analogous to those of the preceding Examples.

Table 10

$$\begin{array}{c} R^1O \quad O \quad R^2 \\ \diagdown \; \| \; \diagup \\ P-N \\ \diagup \quad \diagdown \\ CH_3CH_2CH_2S \quad SO_2R^3 \end{array}$$

| Compound No. | $R^1$ | $R^2$ | $R^3$ | Physical constants |
|---|---|---|---|---|
| 4 | $C_2H_5$ | $CH_3$ | $C_2H_5$ | $n_D^{20}$ 1.4985 |
| 5 | $C_2H_5$ | $CH_3$ | $n\text{-}C_4H_9$ | $n_D^{20}$ 1.4952 |
| 6 | $CH_3$ | $CH_3$ | phenyl | $n_D^{20}$ 1.5245 |
| 7 | $C_2H_5$ | $CH_3$ | phenyl | $n_D^{20}$ 1.5190 |
| 8 | $C_2H_5$ | $CH_3$ | 2,4-dichlorophenyl | $n_D^{20}$ 1.5394 |
| 9 | $C_2H_5$ | $CH_3$ | 4-methylphenyl | $n_D^{20}$ 1.5350 |
| 10 | $C_2H_5$ | $CH_3$ | 4-methoxyphenyl | $n_D^{20}$ 1.5456 |
| 11 | $C_2H_5$ | $CH_3$ | 3-methoxy-4-chlorophenyl | $n_D^{20}$ 1.5572 |
| 12 | $C_2H_5$ | $CH_3$ | 2-nitrophenyl | $n_D^{20}$ 1.5420 |
| 13 | $C_2H_5$ | $C_2H_5$ | $CH_3$ | $n_D^{20}$ 1.4972 |
| 14 | $C_2H_5$ | $i\text{-}C_3H_7$ | $CH_3$ | $n_D^{20}$ 1.5010 |
| 15 | $C_2H_5$ | $i\text{-}C_3H_7$ | $CH_2Cl$ | $n_D^{20}$ 1.5009 |
| 16 | $C_2H_5$ | $i\text{-}C_3H_7$ | phenyl | $n_D^{20}$ 1.5337 |
| 17 | $C_2H_5$ | $n\text{-}C_4H_9$ | $CH_3$ | $n_D^{20}$ 1.4898 |
| 18 | $C_2H_5$ | $-CH_2CH=CH_2$ | $CH_3$ | $n_D^{20}$ 1.5038 |
| 19 | $C_2H_5$ | $-CH_2CH=CH_2$ | phenyl | $n_D^{20}$ 1.5404 |
| 20 | $C_2H_5$ | phenyl | phenyl | $n_D^{20}$ 1.5550 |

Table 10-continued $$\begin{array}{c} R^1O \diagdown \overset{O}{\underset{\|}{P}} - N \diagup R^2 \\ CH_3CH_2CH_2S \diagup \qquad \diagdown SO_2R^3 \end{array}$$

| Compound No. | $R^1$ | $R^2$ | $R^3$ | Physical constants |
|---|---|---|---|---|
| 21 | $C_2H_5$ | —C$_6$H$_4$—Cl (p) | $CH_3$ | $n_D^{20}$ 1.5371 |
| 22 | $C_2H_5$ | —C$_6$H$_4$—CH$_3$ (p) | $CH_3$ | $n_D^{20}$ 1.5367 |
| 23 | $C_2H_5$ | 2-CH$_3$-5-Cl-C$_6$H$_3$— | $CH_3$ | $n_D^{20}$ 1.5380 |
| 24 | $C_2H_5$ | —CH$_2$—C$_6$H$_5$ | $CH_3$ | $n_D^{20}$ 1.5444 |
| 35 | $CH_3$ | $CH_3$ | $CH_3$ | $n_D^{20}$ 1.5030 |
| 36 | $C_2H_5$ | 2-CH$_3$-C$_6$H$_4$—CH$_3$ | $CH_3$ | $n_D^{20}$ 1.5359 |
| 37 | $C_2H_5$ | 2,4-(CH$_3$)$_2$-C$_6$H$_3$— | $CH_3$ | $n_D^{20}$ 1.5300 |
| 38 | $C_2H_5$ | 2,4-Cl$_2$-C$_6$H$_3$— | $CH_3$ | $n_D^{20}$ 1.5390 |
| 39 | $C_2H_5$ | 2-CH$_3$-5-Cl-C$_6$H$_3$— | C$_6$H$_5$ | $n_D^{20}$ 1.5429 |
| 40 | $C_2H_5$ | $CH_3$ | $CH_2Cl$ | $n_D^{20}$ 1.5075 |
| 41 | $C_2H_5$ | $CH_3$ | —C$_6$H$_4$—Br (p) | $n_D^{20}$ 1.5532 |
| 42 | $C_2H_5$ | $CH_3$ | 2,4,5-Cl$_3$-C$_6$H$_2$— | m.p. 99–101 |

EXAMPLE 13

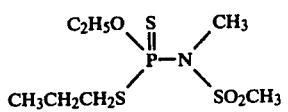

(25)

13.1 g of sodium N-methylmethanesulfonamide was suspended in 100 ml of acetonitrile. 21.9 g of O-ethyl-S-n-propyldithiophosphoryl chloride was added at room temperature and, after gradual heating, the mixture was stirred at 40°–50° C. for 4 hours. After completion of the reaction, acetonitrile was distilled off, toluene was added to the residue, and the mixture was washed with water, with a 1% aqueous solution of sodium hydroxide and again with water. After drying the toluene layer over anhydrous sodium sulfate, toluene was removed at reduced pressure, followed by drying for another hour at 70° C./1 mm Hg to obtain 22 g of O-ethyl-S-n-propyl-N-methyl-N-methane sulfonylphosphoramidodithioate as a colorless oil ($n_D^{20}$ 1.5295).

The following compounds were prepared by methods analogous to those of the preceding Examples.

Table 11

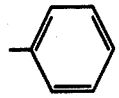

| Compound No. | $R^1$ | $R^2$ | $R^3$ | Physical constants |
|---|---|---|---|---|
| 26 | $C_2H_5$ | $CH_3$ | $C_2H_5$ | $n_D^{20}$ 1.5214 |
| 27 | $C_2H_5$ | $CH_3$ |  | $n_D^{20}$ 1.5440 |
| 28 | $C_2H_5$ | $CH_3$ | 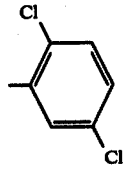 | $n_D^{20}$ 1.5535 |
| 29 | $C_2H_5$ | $CH_3$ | 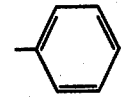 | $n_D^{20}$ 1.5735 |
| 30 | $C_2H_5$ | $C_2H_5$ | $CH_3$ | $n_D^{20}$ 1.5220 |
| 31 | $C_2H_5$ | $i\text{-}C_3H_7$ | $CH_3$ | $n_D^{20}$ 1.5060 |
| 32 | $C_2H_5$ | $-CH_2CH=CH_2$ | $CH_3$ | $n_D^{20}$ 1.5245 |
| 33 | $C_2H_5$ | $-CH_2CH=CH_2$ | 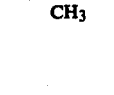 | $n_D^{20}$ 1.5410 |
| 34 | $C_2H_5$ | 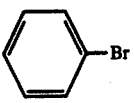 | $CH_3$ | $n_D^{20}$ 1.5530 |

Other compounds of formula I which can be similarly prepared include:

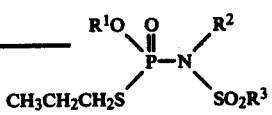

TABLE 12

| Compound No. | $R^1$ | $R^2$ | $R^3$ | X |
|---|---|---|---|---|
| 43 | $CH_3$ | 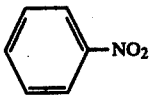 | 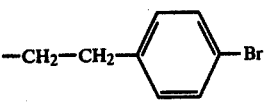 | O |
| 44 | $C_2H_5$ | 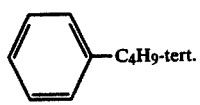 | $-CH_2-CH_2-CH_2-Br$ | O |
| 45 | $CH_3$ | 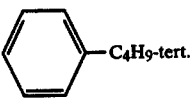 |  | O | and the like.

It will be appreciated that the instant specification and examples are set forth by way of illustration and not limitation, and that various modifications and changes may be made without departing from the spirit and scope of the present invention.

What is claimed is:

1. An O-alkyl-S-n-propyl-N-sulfonylphosphoric acid ester amide of the formula in which
  $R^1$ is methyl or ethyl,
  $R^2$ is $C_1$-$C_6$ alkyl or alkenyl, $C_1$-$C_6$ alkyl substituted by aryl, phenyl, $C_1$-$C_6$ alkylphenyl, or halophenyl, and
  $R^3$ is $C_1$-$C_6$ alkyl, $C_1$-$C_6$ alkyl substituted by halogen, phenyl, $C_1$-$C_6$ alkylphenyl, $C_1$-$C_6$ alkoxyphenyl, halophenyl or nitrophenyl, with the proviso that both $R^2$ and $R^3$ are not simultaneously $C_1$-$C_6$ alkyl.

2. A method of combating insects, acarids or nematodes, which comprises applying to the insects, acarids, or nematodes, or to a habitat thereof an insecticidally, acaricidally or nematicidally effective amount of a compound according to claim 1.

3. A compound according to claim 1, in which R² is alkyl having 1 to 4 carbon atoms, allyl, benzyl, phenyl or phenyl carrying one or two substituents selected from chlorine and methyl, and R³ is alkyl having 1 to 4 carbon atoms, chloromethyl, phenyl or phenyl carrying one to three substituents selected from chlorine, bromine, methyl, methoxy and nitro.

4. The compound according to claim 1, wherein such compound is O-ethyl-S-n-propyl-N-methyl-N-4-chlorobenzenesulfonyl phosphoramidothiolate of the formula

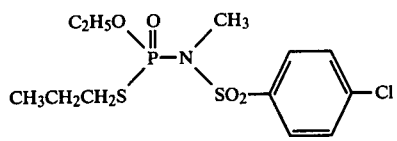
(1)

5. The compound according to claim 1, wherein such compound is O-ethyl-S-n-propyl-N-phenyl-N-methanesulfonylphosphoramidothiolate of the formula

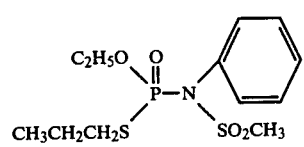
(3)

6. The compound according to claim 1, wherein such compound is O-ethyl-S-n-propyl-N-allyl-N-methanesulfonylphosphoramidothiolate of the formula

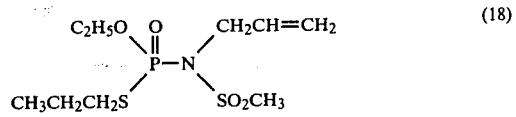
(18)

7. The compound according to claim 1, wherein such compound is O-ethyl-S-n-propyl-N-methyl-N-chloromethanesulfonylphosphoramidothiolate of the formula

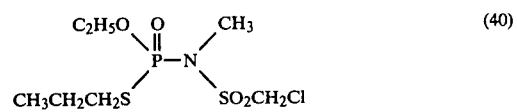
(40)

8. An insecticidal, acaricidal or nematicidal composition containing as active ingredient an insecticidally, acaricidally or nematicidally effective amount of a compound according to claim 1 in admixture with a diluent.

9. The method according to claim 2, in which said compound is
O-ethyl-S-n-propyl-N-methyl-N-4-chlorobenzenesulfonylphosphoramidothiolate,
O-ethyl-S-n-propyl-N-phenyl-N-methanesulfonylphosphoramidothiolate,
O-ethyl-S-n-propyl-N-allyl-N-methanesulfonylphosphoramidothiolate, or
O-ethyl-S-n-propyl-N-methyl-N-chloromethanesulfonylphosphoramidothiolate.

* * * * *